(12) United States Patent
Dolente et al.

(10) Patent No.: US 8,420,633 B2
(45) Date of Patent: Apr. 16, 2013

(54) ARYL-CYCLOHEXYL-TETRAAZABENZO[E] AZULENES

(75) Inventors: Cosimo Dolente, Allschwil (CH); Patrick Schnider, Bottmingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 237 days.

(21) Appl. No.: 13/070,519

(22) Filed: Mar. 24, 2011

(65) Prior Publication Data

US 2011/0245237 A1 Oct. 6, 2011

(30) Foreign Application Priority Data

Mar. 31, 2010 (EP) .................................... 10158871

(51) Int. Cl.
- *A61P 9/00* (2006.01)
- *A61P 15/00* (2006.01)
- *A61P 25/00* (2006.01)
- *A61K 31/5517* (2006.01)
- *C07D 487/04* (2006.01)

(52) U.S. Cl.
USPC .......................................... 514/220; 540/563

(58) Field of Classification Search .................. 514/220; 540/563
See application file for complete search history.

(56) References Cited

U.S. PATENT DOCUMENTS

| | | | |
|---|---|---|---|
| 7,265,104 B2 | 9/2007 | Elliott et al. | |
| 2002/0103373 A1 | 8/2002 | Hockstra et al. | |
| 2011/0245237 A1 | 10/2011 | Dolente et al. | |
| 2011/0251183 A1 | 10/2011 | Dolente et al. | |
| 2011/0263573 A1 | 10/2011 | Dolente et al. | |
| 2011/0263578 A1 | 10/2011 | Dolente et al. | |
| 2011/0275801 A1 | 11/2011 | Dolente et al. | |

FOREIGN PATENT DOCUMENTS

| | | |
|---|---|---|
| EP | 2292621 | 3/2011 |
| KR | 2007/0020462 | 2/2007 |
| WO | 96/22292 | 7/1996 |
| WO | 02/083681 | 10/2002 |
| WO | 2004/074291 | 9/2004 |
| WO | 2005/068466 | 7/2005 |
| WO | 2006/021882 | 3/2006 |
| WO | 2006/114706 | 11/2006 |
| WO | 2006/123242 | 11/2006 |
| WO | 2008/084005 | 7/2008 |
| WO | 2010/057795 | 5/2010 |

OTHER PUBLICATIONS

Gal et al., Progress in Brain Research, Elsevier 139:197-210 XP001205440 ( 2002).
(International Search Report for PCT/EP2011/057368 Jul. 14, 2011).
Ebner et al., Eur. J. Neurosci. 15:384-388 ( 2002).
Altemus et al., Arch. Gen. Psychiatry 49:9-20 ( 1992).
(International Search Report for PCT/EP2009/064804 Jan. 14, 2010).
Regier et al., Br. J. Psychiatry Suppl.:24-28 ( 1998).
(International Search Report PCT/EP2011/056391 Jun. 27, 2011).
Aughton et al., Br. J. Pharmacol.:253 ( 2008).
Robben et al., Am. J. Physiol. Renal. Physiol. 291:F257-270 ( 2006).
Vankerckhoven et al., Eur. J. Pharmacol. 449(1-2):135-141 ( 2002).
(International Search Report PCT/EP2011/056071 May 12, 2011).
Gupta et al., Br. J. Pharmacol. 155:118-126 ( 2008).
Raskind et al., Biol. Psychiatry 22:453-462 ( 1987).
Neumann, J. Neuroendocrinol. 20:858-865 ( 2008).
Bielsky et al., Neuropsychopharmacology 29:483-493 ( 2004).
Brouard et al., Bjog. 107:614-619 ( 2000).
(International Search Report for PCT/EP2011/054582 Mar. 25, 2011).
Michelini et al., Ann. NY Academy Science 897:198-211 ( 1999).
(International Search Report PCT/EP2009/065354 Feb. 8, 2010).
Liebsch et al., Regulatory Peptides 59(2):229-239 ( 1995).
Yirmiya et al., 11:488-494 ( 2006).
(International Search Report PCT/EP2011/055516 May 23, 2011).
Kendler et al., Arch. Gen. Psychiatry 60:789-796 ( 2003).
Thompson et al., Psychoneuroendocrinology 29:35-48 ( 2004).
(Opposition in Costa Rican Appl 2011-0220 Sep. 20, 2011).

*Primary Examiner* — Brenda Coleman
(74) *Attorney, Agent, or Firm* — George W. Johnston; Patricia S. Rocha-Tramaloni; Kimberly J. Prior

(57) ABSTRACT

The present invention is concerned with aryl-cyclohexyl-tetraazabenzo[e]azulenes of formula I

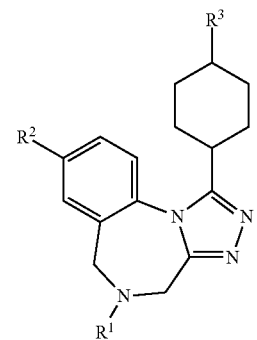

I wherein $R^1$, $R^2$ and $R^3$ are as described herein. The invention further provides methods for the manufacture of such compounds and pharmaceutical compositions containing them. The compounds according to the invention act as V1a receptor modulators, and in particular as V1a receptor antagonists. The compounds are useful as therapeutics acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

14 Claims, No Drawings

ARYL-CYCLOHEXYL-TETRAAZABENZO[E] AZULENES

PRIORITY TO RELATED APPLICATION(S)

This application claims the benefit of European Patent Application No. 10158871.3, filed Mar. 31, 2010, which is hereby incorporated by reference in its entirety.

FIELD OF THE INVENTION

The present invention is concerned with aryl-cyclohexyl-tetraazabenzo[e]azulenes, which act as V1a receptor modulators, and in particular as V1a receptor antagonists, their manufacture, pharmaceutical compositions containing them and their use as medicaments.

BACKGROUND OF THE INVENTION

Vasopressin is a 9 amino acid peptide mainly produced by the paraventricular nucleus of the hypothalamus. In the periphery vasopressin acts as a neurohormone and stimulates vasoconstriction, glycogenolysis and antidiuresis.

Three vasopressin receptors, all belonging to the class I G-protein coupled receptors, are known. The V1a receptor is expressed in the brain, liver, vascular smooth muscle, lung, uterus and testis, the V1b or V3 receptor is expressed in the brain and pituitary gland, the V2 receptor is expressed in the kidney where it regulates water reabsorption and mediates the antidiuretic effects of vasopressin (Robben, et al. (2006). Am J Physiol Renal Physiol. 291, F257-70, "Cell biological aspects of the vasopressin type-2 receptor and aquaporin 2 water channel in nephrogenic diabetes insipidus"). Compounds with activity at the V2 receptor can therefore cause side-effects on blood homeostasis.

The oxytocin receptor is related to the Vasopressin receptor family and mediates the effects of the neurohormone oxytocin in the brain and the periphery. Oxytocin is believed to have central anxiolytic effects (Neumann (2008). J. Neuroendocrinol. 20, 858-65, "Brain oxytocin: a key regulator of emotional and social behaviors in both females and males"). Central oxytocin receptor antagonism might therefore lead to anxiogenic effects, which are regarded as undesired side-effects.

In the brain vasopressin acts as a neuromodulator and is elevated in the amygdala during stress (Ebner, et al. (2002). Eur J. Neurosci. 15, 384-8. "Forced swimming triggers vasopressin release within the amygdala to modulate stress-coping strategies in rats"). It is known that stressful life events can trigger major depression and anxiety (Kendler, et al. (2003). Arch Gen Psychiatry. 60, 789-96, "Life Event Dimensions of Loss, Humiliation, Entrapment, and Danger in the Prediction of Onsets of Major Depression and Generalized Anxiety") and that both have very high comorbidity, with anxiety often preceding major depression (Regier, et al. (1998). Br J Psychiatry Suppl. 24-8, "Prevalence of anxiety disorders and their comorbidity with mood and addictive disorders"). The V1a receptor is extensively expressed in the brain and particularly in limbic areas like the amygdala, lateral septum and hippocampus which are playing an important role in the regulation of anxiety. Indeed V1a knock-out mice show a reduction in anxious behavior in the plus-maze, open field and light-dark box (Bielsky, et al. (2004). Neuropsychopharmacology. 29, 483-93, "Profound impairment in social recognition and reduction in anxiety-like behavior in vasopressin V1a receptor knockout mice"). The downregulation of the V1a receptor using antisense oligonucleotide injection in the septum also causes a reduction in anxious behavior (Landgraf, et al. (1995). Regul Pept. 59, 229-39. "V1 vasopressin receptor antisense oligodeoxynucleotide into septum reduces vasopressin binding, social discrimination abilities, and anxiety-related behavior in rats"). Vasopressin or the V1a receptor are also implicated in other neuropyschological disorders: genetic studies recently linked sequence polymorphism in the promoter of the human V1a receptor to autistic spectrum disorders (Yirmiya, et al. (2006). 11, 488-94, "Association between the arginine vasopressin 1a receptor (AVPR1a) gene and autism in a family-based study: mediation by socialization skills"), intranasal administration of vasopressin was shown to influence aggression in human males (Thompson, et al. (2004). Psychoneuroendocrinology. 29, 35-48, "The effects of vasopressin on human facial responses related to social communication") and vasopressin levels were found to be elevated in schizophrenic patients (Raskind, et al. (1987). Biol Psychiatry. 22, 453-62, "Antipsychotic drugs and plasma vasopressin in normals and acute schizophrenic patients") and patients with obsessive-compulsive disorder (Altemus, et al. (1992). Arch Gen Psychiatry. 49, 9-20, "Abnormalities in the regulation of vasopressin and corticotropin releasing factor secretion in obsessive-compulsive disorder").

The V1a receptor is also mediating the cardiovascular effects of vasopressin in the brain by centrally regulating blood pressure and heart rate in the solitary tract nucleus (Michelini and Morris (1999). Ann N Y Acad. Sci. 897, 198-211, "Endogenous vasopressin modulates the cardiovascular responses to exercise"). In the periphery it induces the contraction of vascular smooth muscles and chronic inhibition of the V1a receptor improves hemodynamic parameters in myocardial infarcted rats (Van Kerckhoven, et al. (2002). Eur J Pharmacol. 449, 135-41, "Chronic vasopressin V(1A) but not V(2) receptor antagonism prevents heart failure in chronically infarcted rats"). Hence, V1a antagonists with improved penetration through the blood-brain barrier are expected to be of advantage.

A vasopressin V1a receptor antagonist was shown to be effective in reducing dysmenorrhea in the clinic (Brouard, et al. (2000). Bjog. 107, 614-9, "Effect of SR49059, an orally active V1a vasopressin receptor antagonist, in the prevention of dysmenorrhea"). V1a receptor antagonism has also been implicated in the treatment of female sexual dysfunction (Aughton, et al. (2008). Br J Pharmacol. doi:10.1038/bjp.2008.253, "Pharmacological profiling of neuropeptides on rabbit vaginal wall and vaginal artery smooth muscle in vitro"). In a recent study V1a receptor antagonists were suggested to have a therapeutic role in both erectile dysfunction and premature ejaculation (Gupta, et al. (2008). Br J Pharmacol. 155, 118-26, "Oxytocin-induced contractions within rat and rabbit ejaculatory tissues are mediated by vasopressin V(1A) receptors and not oxytocin receptors").

SUMMARY OF THE INVENTION

The present invention provides compounds of formula I useful for acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

In particular, the present invention provides compounds of formula I

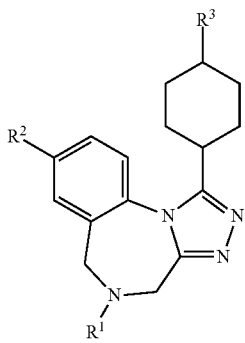

wherein $R^1$, $R^2$ and $R^3$ are as described in herewithin.

DETAILED DESCRIPTION OF THE INVENTION

The present invention provides compounds which act as V1a receptor modulators, and in particular as V1a receptor antagonists. The present invention further provides selective inhibitors of the V1a receptor. It is expected that selectivity affords a low potential to cause unwanted off-target related side effects such as discussed above.

Such V1a antagonists are useful as therapeutics acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior. Particular indications with regard to the present invention are the treatment of anxiety, depressive disorders, obsessive compulsive disorder, autistic spectrum disorders, schizophrenia, and aggressive behavior.

The V1a activity can be detected as described in the experimental section.

The following definitions of the general terms used in the present description apply irrespective of whether the terms in question appear alone or in combination.

As used herein, the term "$C_{1-6}$alkyl", alone or in combination with other groups, stands for a hydrocarbon radical that is linear or branched, with single or multiple branching, containing 1 to 6 carbon atoms, for example, methyl (Me), ethyl (Et), propyl, isopropyl (i-propyl), n-butyl, i-butyl (iso-butyl), 2-butyl (sec-butyl), t-butyl (tert-butyl) and the like. Particular alkyl groups are groups with 1 to 4 carbon atoms. More particular are methyl, ethyl, propyl, isopropyl and t-butyl. Most particular is methyl.

The term "$C_{1-6}$-alkoxy", alone or in combination with other groups, denotes a group —O—R' wherein R' is $C_{1-6}$alkyl as defined above, for example methoxy, ethoxy, propoxy, tert-butoxy and the like. Particular alkoxy groups are groups with 1 to 4 carbon atoms ($C_{1-4}$-alkoxy). Most particular is methoxy.

The term "aryl" refers to an aromatic carbocyclic group containing 6 to 14, particularly 6 to 10, carbon atoms and having at least one aromatic ring or multiple condensed rings in which at least one ring is aromatic. Examples include phenyl (Ph), benzyl, naphthyl, biphenyl, anthryl, azalenyl or indanyl. Particular are phenyl and naphthyl, more particular is phenyl.

The term "heteroaryl", alone or in combination with other groups, refers to a cyclic aromatic group having a single 5 to 6 membered ring and containing 1, 2 or 3 heteroatoms, in which group at least one heterocyclic ring is aromatic. The term "6-membered heteroaryl" refers to a monocyclic aromatic group having a single 6 membered ring, and containing 1, 2 or 3 heteroatoms independently selected from O, S and N. Particular single 6 membered rings have 1 or 2 N. Examples include pyridinyl, pyrimidinyl, pyrazinyl, pyridazinyl, thiazinyl, oxazinyl and the like. Particular single 6 membered rings are pyridinyl, pyrazinyl, pyridazinyl and pyrimidinyl. Specific "6-membered heteroaryl" are attached via a carbon atom to the cyclohexyl-moiety. Particular is pyridinyl, more particular pyridin-2-yl. The term "5-membered heteroaryl" refers to a monocyclic aromatic group having a single 5 membered ring, and containing 1, 2 or 3 heteroatoms independently selected from O, S and N. Particular single 5 membered rings have 2 N or 1 O and 1 N. Examples include thiazolyl, isoxazolyl, isothiazolyl, oxadiazolyl, thiadiazolyl and the like. Particular are pyridinyl, pyrazinyl, pyridazinyl and pyrimidinyl. Specific "5-membered heteroaryl" are attached via a carbon atom to the cyclohexyl moiety.

The term "cyano" denotes the group —CN.
The term "hydroxy" denotes the group —OH.
The term "acetonyl" denotes the group —$CH_2$—C(O)—$CH_3$.
The term "acetyl" denotes the group —C(O)$CH_3$.
The term "sulfonyl" denotes the group —S(=O)$_2$—$CH_3$.
The term "halogen", alone or in combination with other groups, denotes chlorine (Cl), iodine (I), fluorine (F) and bromine (Br). Specific halogens are fluorine and chlorine, particular is chlorine.

The term "halogen-$C_{1-6}$alkyl" refers to a $C_{1-6}$alkyl group substituted by one or multiple halogen, preferably fluoro, for example the following groups: $CF_3$, $CHF_2$, $CH_2F$, $CH_2CF_3$, $CH_2CH_2CF_3$, $CHF_2CF_2$, and the like. Particular groups are $CF_3$— and $CF_3CH_2$—, more particular is $CF_3$—.

The term "hydroxy-$C_{1-6}$alkyl" refers to a $C_{1-6}$alkyl group substituted by one or multiple hydroxy, for example the following groups: hydroxymethyl-, 2-hydroxyethyl-, 2-hydroxy-1-methyl-ethyl- or 2-hydroxypropyl- and the like.

The term "cyano-$C_{1-6}$alkyl" refers to a $C_{1-6}$alkyl group substituted by one or multiple cyano, for example the following groups: cyano-methyl-, 2-cyano-ethyl-, 2-cyano-1-methyl-ethyl- or 2-cyano-propyl- and the like.

The term "halogen-$C_{1-6}$alkoxy" refers to a $C_{1-6}$alkoxy group substituted by one or multiple halogen, for example the following groups: F—$CH_2$—O—.

When indicating the number of substituents, the term "one or more" means from one substituent to the highest possible number of substitution, i.e. replacement of one hydrogen up to replacement of all hydrogens by substituents. Thereby, one, two or three substituents are particular. Even more particular are one or two substituents or one substituent.

The term "pharmaceutically acceptable salts" refers to salts that are suitable for use in contact with the tissues of humans and animals without undue toxicity, irritation, allergic response, and the like. Examples of suitable salts with inorganic and organic acids are, but are not limited to, hydrochloric acid, nitric acid, sulphuric acid, phosphoric acid, sulphuric acid, citric acid, formic acid, fumaric acid, maleic acid, lactic acid, malic acid, acetic acid, succinic acid, tartaric acid, methane-sulfonic acid, p-toluenesulphonic acid, trifluoroacetic acid and the like. Specific is hydrochloric acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

"Therapeutically effective amount" means an amount that is effective to prevent, alleviate or ameliorate symptoms of disease or prolong the survival of the subject being treated.

The following table lists abbreviations used within the present document.

TABLE 1

Abbreviations

| | |
|---|---|
| (BOC)$_2$O | di-tert-butyl pyrocarbonate |
| (COCl)$_2$ | oxalyl (di)chloride |
| AcOH | acetic acid |
| CH$_2$Cl$_2$ | dichloromethane |
| DMAP | 4-(dimethylamino)-pyridine |
| DMSO | dimethylsulfoxide |
| EDTA | ethylendiamin tetraacetate |
| EtN$_3$ | triethylamine |
| EtOAc | ethyl acetate |
| EtOH | ethanol |
| HEPES | 2-(4-(2-hydroxyethyl)-1-piperazinyl)-ethanesulfonic acid |
| HPLC | high performance liquid crystallography |
| K$_3$PO$_4$ | potassium phosphate |
| Lawesson's reagent | 2,4-bis-(4-methoxyphenyl)-1,3,2,4-dithiadiphosphetane-2,4-disulfide |
| MeOH | methanol |
| MS | mass spectroscopy |
| NaOEt | sodium ethoxide |
| NaOH | sodium hydroxide |
| n-BuOH | n-butanol |
| NMR | nuclear magnetic resonance |
| Pd(PPh)$_3$ | tetrakis(triphenylphosphine)palladium(0) |
| PtO$_2$ | platinum oxide |
| RNA | ribonucleic acid |
| RT | room temperature |
| RT-PCR | reverse transcription-polymerase chain reaction |
| SOCl$_2$ | thionyl chloride |
| t-BuOK | potassium-tert-butoxide |
| THF | tetrahydrofunran |
| Tris | Tris(hydroxymethyl)-aminomethane |
| ZnBr$_2$ | zinc bromide |

The invention also provides pharmaceutical compositions, methods of using, and methods of preparing the aforementioned compounds.

While the present invention has been described with reference to the specific embodiments thereof, it should be understood by those skilled in the art that various changes can be made and equivalents can be substituted without departing from the true spirit and scope of the invention. In addition, many modifications can be made to adapt a particular situation, material, composition of matter, process, process step or steps, to the objective spirit and scope of the present invention. All such modifications are intended to be within the scope of the claims appended hereto. All separate embodiments can be combined.

The compounds of formula I can contain asymmetric carbon atoms. Accordingly, the present invention includes all stereoisomeric forms of the compounds of formula I, including each of the individual stereoisomer and mixtures thereof, i.e. their individual optical isomers and mixtures thereof. Additional asymmetric centers can be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to comprehend all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric centre of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

This applies in particular to the aryl-head group (HG) of the compounds of formula I, namely

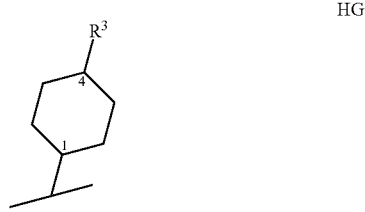

HG wherein at least the carbon atoms 1 and 4 are asymmetric carbon atoms and R$^3$ could further comprise asymmetric carbon atoms. It is to be understood that present invention includes all individual stereoisomers of head groups and mixtures thereof.

In particular, these head groups HG are

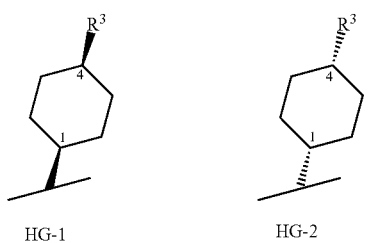

HG-1          HG-2 trans

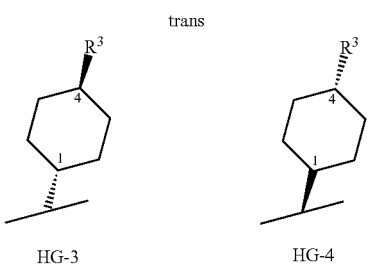

HG-3          HG-4 cis

It is further understood that all embodiments of the invention as described herein can be combined with each other.

In detail, the present invention is concerned with compounds of formula I

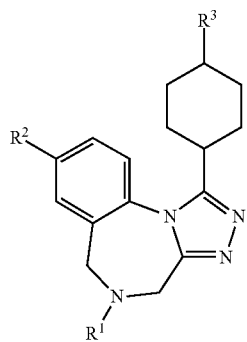

wherein
R¹ is selected from the group consisting of
i) H,
ii) —C$_{1-6}$-alkyl, unsubstituted or substituted by 1 to 5 substituents individually selected from the group consisting of OH, halogen, cyano and C$_{1-6}$-alkoxy,
iii) —(CH$_2$)$_p$—R⁴, wherein
  p is 0 or 1,
  R⁴ is phenyl or 5- or 6-membered heteroaryl, each of which is unsubstituted or substituted by 1 to 5 substituents individually selected from the group consisting of OH, halogen, cyano, C$_{1-6}$-alkoxy, halogen-C$_{1-6}$-alkyl, halogen-C$_{1-6}$-alkoxy and hydroxy-C$_{1-6}$-alkyl,
iv) —S(O)$_2$—C$_{1-6}$-alkyl, wherein the C$_{1-6}$-alkyl is unsubstituted or substituted by 1 to 5 substituents individually selected from the group consisting of OH, halogen, cyano and C$_{1-6}$-alkoxy,
v) —C(O)—C$_{1-6}$-alkyl, wherein the C$_{1-6}$-alkyl is unsubstituted or substituted by 1 to 5 substituents individually selected from the group consisting of OH, halogen, cyano and C$_{1-6}$-alkoxy, and
vi) —C(O)O—C$_{1-6}$-alkyl, wherein the C$_{1-6}$-alkyl is unsubstituted or substituted by 1 to 5 substituents individually selected from the group consisting of OH, halogen, cyano and C$_{1-6}$-alkoxy;
R² is selected from the group consisting of hydrogen and halogen; and
R³ is aryl, unsubstituted or substituted by 1 to 5 substituents individually selected from the group consisting of OH, halogen, cyano, C$_{1-6}$-alkyl, C$_{1-6}$-alkoxy, halogen-C$_{1-6}$-alkyl, halogen-C$_{1-6}$-alkoxy and hydroxy-C$_{1-6}$-alkyl;
or a pharmaceutically acceptable salt thereof.

One specific embodiment provides compounds where R¹ is selected from the group consisting of H, —C$_{1-6}$-alkyl, hydroxy-C$_{1-6}$-alkyl, —CH$_2$-6-membered heteroaryl, -6-membered heteroaryl, —S(O)$_2$—C$_{1-6}$-alkyl, —C(O)—C$_{1-6}$-alkyl and —C(O)O—C$_{1-6}$-alkyl.

One specific embodiment provides compounds where R¹ is selected from the group consisting of H, —C$_{1-6}$-alkyl, hydroxy-C$_{1-6}$-alkyl, —CH$_2$-6-membered heteroaryl and —C(O)—C$_{1-6}$-alkyl.

One specific embodiment provides compounds where R¹ is selected from the group consisting of 2-hydroxy-ethyl-, acetonyl, H, isopropyl, methyl, methyl-sulfonyl-, pyridin-2-yl, pyridin-2-yl-methyl- and t-butyl-acetyl-.

One specific embodiment provides compounds where R¹ is selected from the group consisting of H, methyl, acetonyl, isopropyl, pyridin-2-yl-methyl- and 2-hydroxy-ethyl.

One specific embodiment provides compounds where R¹ is H.

One specific embodiment provides compounds where R¹ is —C$_{1-6}$-alkyl.

One specific embodiment provides compounds where R¹ is methyl.

One specific embodiment provides compounds where R¹ is isopropyl.

One specific embodiment provides compounds where R¹ is —C$_{1-6}$-alkyl substituted by OH.

One specific embodiment provides compounds where R¹ is 2-hydroxy-ethyl.

One specific embodiment provides compounds where R¹ is 6-membered heteroaryl.

One specific embodiment provides compounds where R¹ is pyridin-2-yl.

One specific embodiment provides compounds where R¹ is —CH$_2$—R⁴, and R⁴ is 6-membered heteroaryl.

One specific embodiment provides compounds where R¹ is pyridin-2-yl-methyl-.

One specific embodiment provides compounds where R¹ is S(O)$_2$—C$_{1-6}$-alkyl.

One specific embodiment provides compounds where R¹ is methyl-sulfonyl-.

One specific embodiment provides compounds where R¹ is —C(O)—C$_{1-6}$-alkyl.

One specific embodiment provides compounds where R¹ is acetonyl.

One specific embodiment provides compounds where R¹ is C(O)O—C$_{1-6}$-alkyl.

One specific embodiment provides compounds where R¹ is t-butyl-acetyl-.

One specific embodiment provides compounds where R² is hydrogen.

One specific embodiment provides compounds where R² is halogen.

One specific embodiment provides compounds where R² is chloro.

One specific embodiment provides compounds where R³ is aryl, unsubstituted or substituted by 1 to 2 substituents individually selected from the group consisting of halogen, cyano, C$_{1-6}$-alkyl, C$_{1-6}$-alkoxy and halogen-C$_{1-6}$-alkoxy.

One specific embodiment provides compounds where R³ is 2-Cl, 3-F-Ph-, 2-MeO, 3-F-Ph-, 2-Me-Ph-, 3-CF$_3$—O-Ph-, 3-CN-Ph-, 4-F-Ph-, naphth-1-yl or Ph.

One specific embodiment provides compounds where R³ is aryl.

One specific embodiment provides compounds where R³ is phenyl or naphth-1-yl.

One specific embodiment provides compounds where R³ is phenyl.

One specific embodiment provides compounds where R³ is naphth-1-yl.

One specific embodiment provides compounds where R³ is aryl substituted by 1-2 halogen, cyano, C$_{1-6}$-alkyl, C$_{1-6}$-alkoxy or halogen-C$_{1-6}$-alkoxy.

One specific embodiment provides compounds where R³ is phenyl substituted by 1-2 halogen, cyano, C$_{1-6}$-alkyl, C$_{1-6}$-alkoxy or halogen-C$_{1-6}$-alkoxy.

One specific embodiment provides compounds where R³ is phenyl substituted by 1-2 halogen.

One specific embodiment provides compounds where R³ is 2-Cl, 3-F-Ph-.

One specific embodiment provides compounds where $R^3$ is 4-F-Ph-.

One specific embodiment provides compounds where $R^3$ is 2-MeO, 3-F-Ph-.

One specific embodiment provides compounds where $R^3$ is 2-Me-Ph-.

One specific embodiment provides compounds where $R^3$ is 3-CF$_3$—O-Ph-.

One specific embodiment provides compounds where $R^3$ is 3-CN-Ph-.

Examples for the compound according to the invention are shown in the experimental part and the table below.

TABLE 1 structures of selected examples

| Ex | Structure |
|---|---|
| 1 | 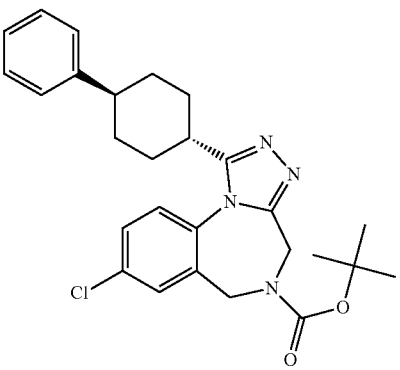 [SMILES: CC(C)(C)OC(=O)N1Cc2cc(Cl)ccc2-n2c(nnc2[C@H]2CC[C@H](c3ccccc3)CC2)C1] |
| 2 | 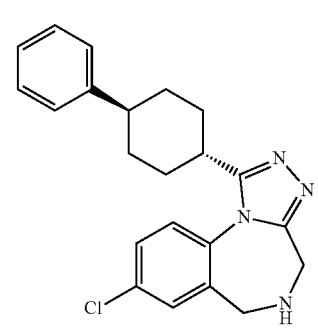 HCl |
| 3 | 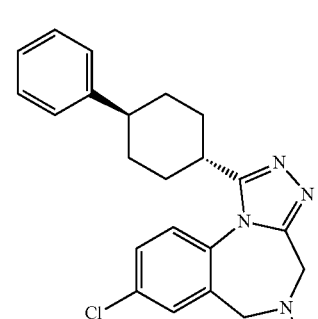 |
| 4 | 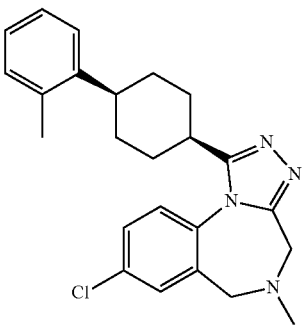 [SMILES: Cc1ccccc1[C@H]1CC[C@@H](c2nnc3n2-c2ccc(Cl)cc2CN(C)C3)CC1] |
| 5 | 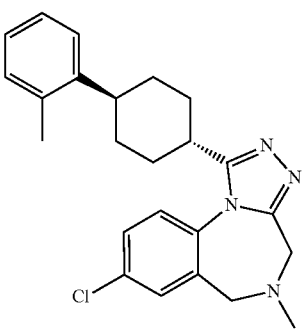 [SMILES: Cc1ccccc1[C@H]1CC[C@H](c2nnc3n2-c2ccc(Cl)cc2CN(C)C3)CC1] |
| 6 | 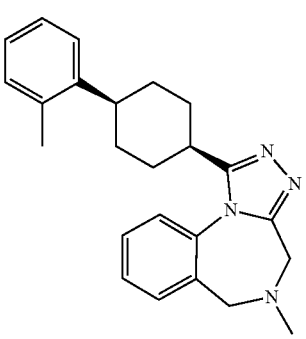 [SMILES: Cc1ccccc1[C@H]1CC[C@@H](c2nnc3n2-c2ccccc2CN(C)C3)CC1] |
| 7 | 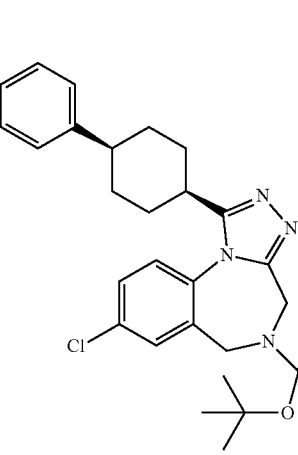 |

TABLE 1-continued
structures of selected examples
| Ex | Structure |
|---|---|
| 8 | 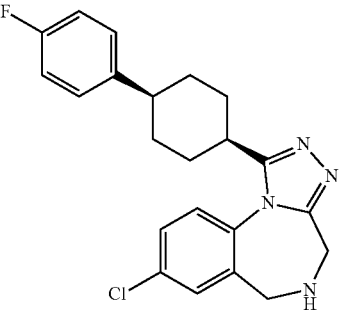 HCl |
| 9 | 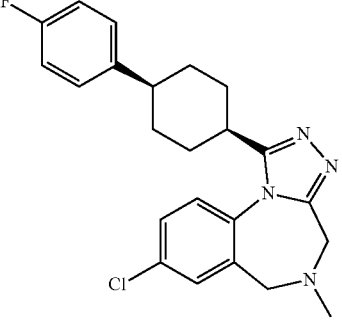 |
| 10 | 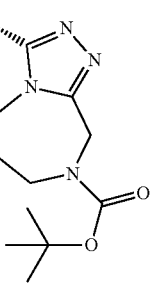 |
| 11 | 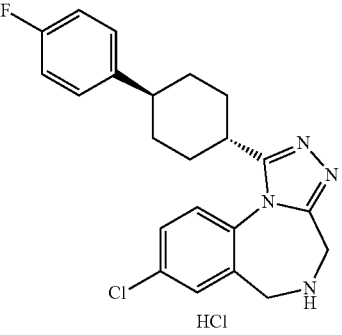 [SMILES: Fc1ccc([C@H]2CC[C@H](c3nnc4n3-c3ccc(Cl)cc3CNC4)CC2)cc1 ; Cl] HCl |
| 12 | 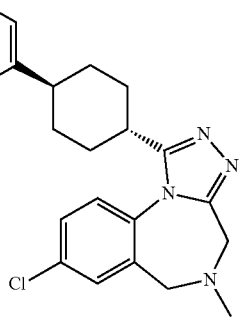 |
| 13 | 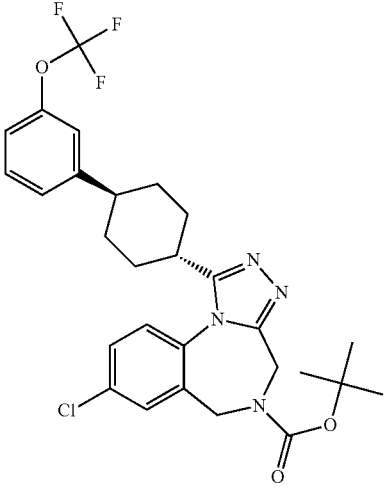 [SMILES: CC(C)(C)OC(=O)N1Cc2cc(Cl)ccc2-n2c(nnc2[C@H]2CC[C@H](c3cccc(OC(F)(F)F)c3)CC2)C1] |
| 14 | 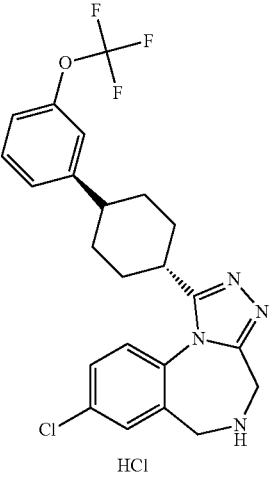 HCl |

TABLE 1-continued
structures of selected examples
| Ex | Structure |
|---|---|
| 15 | 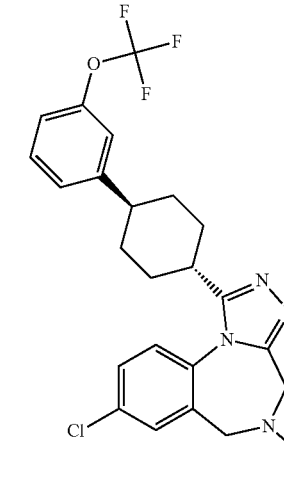 |
| 16 | 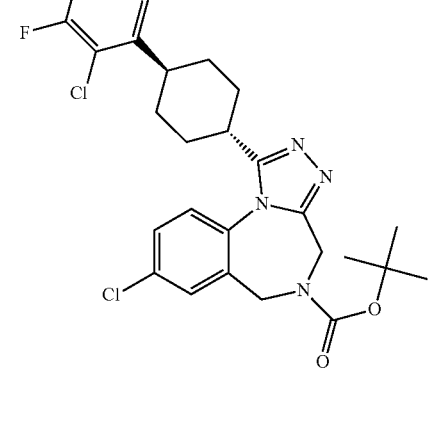 |
| 17 | 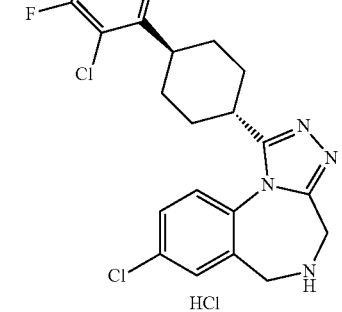 |
| 18 | 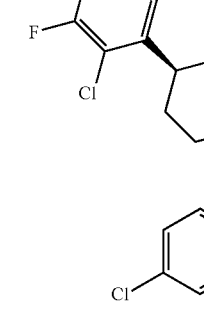 |
| 19 | 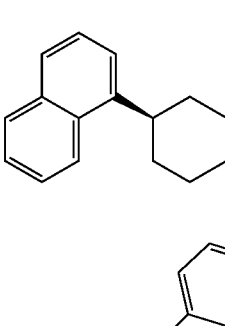 |
| 20 | 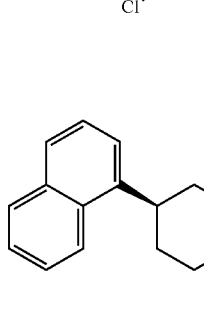 |
| 21 | 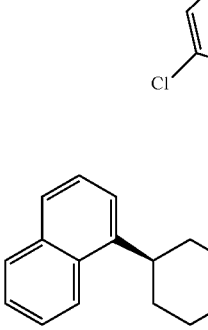 |

TABLE 1-continued
structures of selected examples
| Ex | Structure |
|---|---|
| 22 | 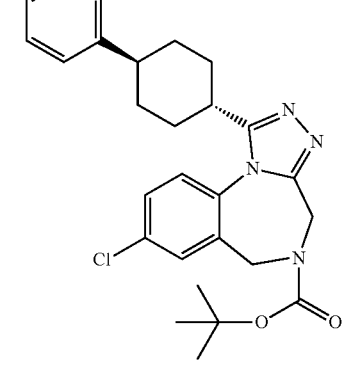 |
| 23 | 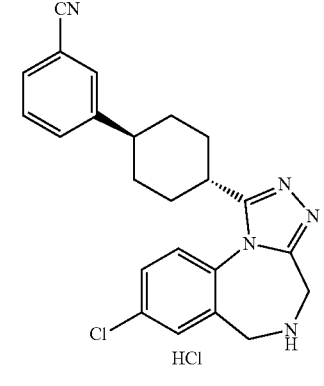 |
| 24 | 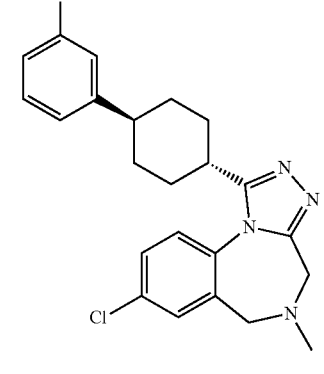 |
| 25 | 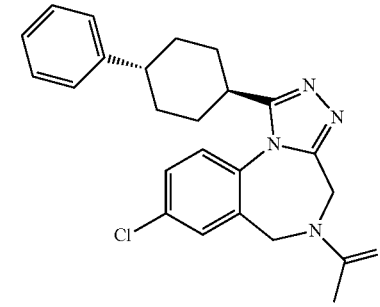 |
| 26 | 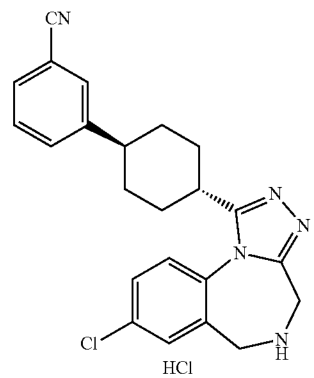 [SMILES: N#Cc1cccc([C@H]2CC[C@H](c3nnc4n3-c3ccc(Cl)cc3CNC4)CC2)c1 ; Cl] |
| 27 | 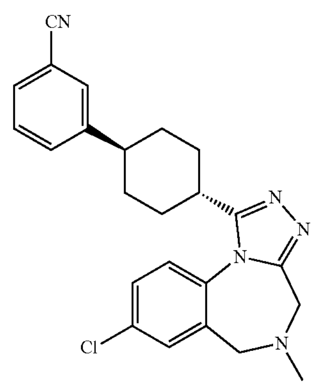 [SMILES: CN1Cc2cc(Cl)ccc2-n2c(nnc2[C@H]2CC[C@H](c3cccc(C#N)c3)CC2)C1] |
| 28 | 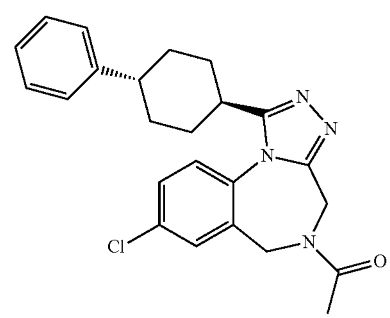 [SMILES: CC(=O)N1Cc2cc(Cl)ccc2-n2c(nnc2[C@H]2CC[C@H](c3ccccc3)CC2)C1] |

TABLE 1-continued structures of selected examples

| Ex | Structure |
|---|---|
| 29 | 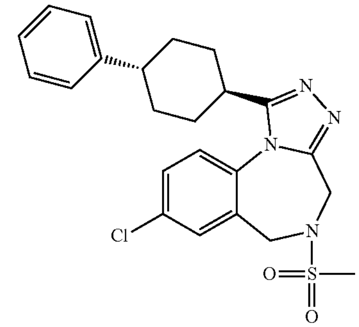 [SMILES: CS(=O)(=O)N1Cc2cc(Cl)ccc2-n2c(nnc2[C@H]2CC[C@H](c3ccccc3)CC2)C1] |
| 30 | 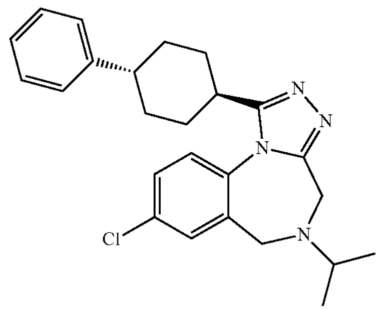 [SMILES: CC(C)N1Cc2cc(Cl)ccc2-n2c(nnc2[C@H]2CC[C@H](c3ccccc3)CC2)C1] |
| 31 | 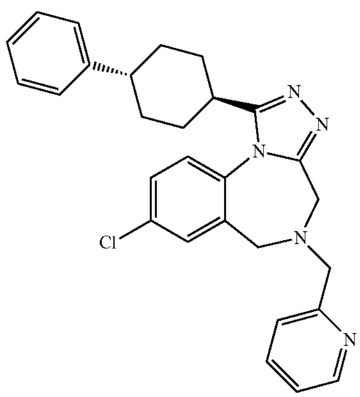 [SMILES: Clc1ccc2c(c1)CN(Cc1ccccn1)Cc1nnc([C@H]3CC[C@H](c4ccccc4)CC3)n1-2] |
| 32 | 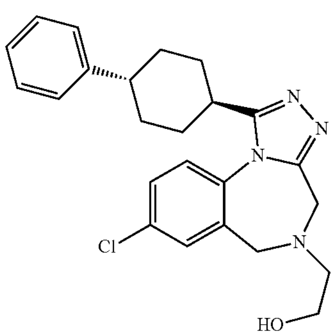 [SMILES: OCCN1Cc2cc(Cl)ccc2-n2c(nnc2[C@H]2CC[C@H](c3ccccc3)CC2)C1] |

TABLE 1-continued structures of selected examples

| Ex | Structure |
|---|---|
| 33 | |

Specific compounds of the invention are shown in the examples. Particular compounds are
(trans)-8-Chloro-1-(4-phenyl-cyclohexyl)-4H,6H-2,3,5,10b-tetraaza-benzo[e]azulene-5-carboxylic acid tert-butyl ester,
(trans)-8-Chloro-1-(4-phenyl-cyclohexyl)-5,6-dihydro-4H-2,3,5,10b-tetraaza-benzo[e]azulene,
(trans)-8-Chloro-5-methyl-1-(4-phenyl-cyclohexyl)-5,6-dihydro-4H-2,3,5,10b-tetraaza-benzo[e]azulene,
(cis)-8-Chloro-5-methyl-1-(4-o-tolyl-cyclohexyl)-5,6-dihydro-4H-2,3,5,10b-tetraaza-benzo[e]azulene,
(trans)-8-Chloro-5-methyl-1-(4-o-tolyl-cyclohexyl)-5,6-dihydro-4H-2,3,5,10b-tetraaza-benzo[e]azulene,
(cis)-5-Methyl-1-(4-o-tolyl-cyclohexyl)-5,6-dihydro-4H-2,3,5,10b-tetraaza-benzo[e]azulene,
(cis)-8-Chloro-1-[4-(4-fluoro-phenyl)-cyclohexyl]-4H,6H-2,3,5,10b-tetraaza-benzo[e]azulene-5-carboxylic acid tert-butyl ester,
(cis)-8-Chloro-1-[4-(4-fluoro-phenyl)-cyclohexyl]-5,6-dihydro-4H-2,3,5,10b-tetraaza-benzo[e]azulene,
(cis)-8-Chloro-1-[4-(4-fluoro-phenyl)-cyclohexyl]-5-methyl-5,6-dihydro-4H-2,3,5,10b-tetraaza-benzo[e]azulene,
(trans)-8-Chloro-1-[4-(4-fluoro-phenyl)-cyclohexyl]-4H,6H-2,3,5,10b-tetraaza-benzo[e]azulene-5-carboxylic acid tert-butyl ester,
(trans)-8-Chloro-1-[4-(4-fluoro-phenyl)-cyclohexyl]-5,6-dihydro-4H-2,3,5,10b-tetraaza-benzo[e]azulene,
(trans)-8-Chloro-1-[4-(4-fluoro-phenyl)-cyclohexyl]-5-methyl-5,6-dihydro-4H-2,3,5,10b-tetraaza-benzo[e]azulene,
(trans)-8-Chloro-1-[4-(3-trifluoromethoxy-phenyl)-cyclohexyl]-4H,6H-2,3,5,10b-tetraaza-benzo[e]azulene-5-carboxylic acid tert-butyl ester,
(trans)-8-Chloro-1-[4-(3-trifluoromethoxy-phenyl)-cyclohexyl]-5,6-dihydro-4H-2,3,5,10b-tetraaza-benzo[e]azulene,
(trans)-8-Chloro-5-methyl-1-[4-(3-trifluoromethoxy-phenyl)-cyclohexyl]-5,6-dihydro-4H-2,3,5,10b-tetraaza-benzo[e]azulene,
(trans)-8-Chloro-1-[4-(2-chloro-3-fluoro-phenyl)-cyclohexyl]-4H,6H-2,3,5,10b-tetraaza-benzo[e]azulene-5-carboxylic acid tert-butyl ester,
(trans)-8-Chloro-1-[4-(2-chloro-3-fluoro-phenyl)-cyclohexyl]-5,6-dihydro-4H-2,3,5,10b-tetraaza-benzo[e]azulene,
(trans)-8-Chloro-1-[4-(2-chloro-3-fluoro-phenyl)-cyclohexyl]-5-methyl-5,6-dihydro-4H-2,3,5,10b-tetraaza-benzo[e]azulene, (trans)-8-Chloro-1-(4-naphthalen-1-yl-cyclohexyl)-4H,6H-2,3,5,10b-tetraaza-benzo[e]azulene-5-carboxylic acid tert-butyl ester,
(trans)-8-Chloro-1-(4-naphthalen-1-yl-cyclohexyl)-5,6-dihydro-4H-2,3,5,10b-tetraaza-benzo[e]azulene,
(trans)-8-Chloro-5-methyl-1-(4-naphthalen-1-yl-cyclohexyl)-5,6-dihydro-4H-2,3,5,10b-tetraaza-benzo[e]azulene,
(trans)-8-Chloro-1-[4-(5-fluoro-2-methoxy-phenyl)-cyclohexyl]-4H,6H-2,3,5,10b-tetraaza-benzo[e]azulene-5-carboxylic acid tert-butyl ester,
(trans)-8-Chloro-1-[4-(5-fluoro-2-methoxy-phenyl)-cyclohexyl]-5,6-dihydro-4H-2,3,5,10b-tetraaza-benzo[e]azulene,
(trans)-8-Chloro-1-[4-(5-fluoro-2-methoxy-phenyl)-cyclohexyl]-5-methyl-5,6-dihydro-4H-2,3,5,10b-tetraaza-benzo[e]azulene,
(trans)-8-Chloro-1-[4-(3-cyano-phenyl)-cyclohexyl]-4H,6H-2,3,5,10b-tetraaza-benzo[e]azulene-5-carboxylic acid tert-butyl ester,
(trans)-3-[4-(8-Chloro-5,6-dihydro-4H-2,3,5,10b-tetraaza-benzo[e]azulen-1-yl)-cyclohexyl]-benzonitrile,
(trans)-3-[4-(8-Chloro-5-methyl-5,6-dihydro-4H-2,3,5,10b-tetraaza-benzo[e]azulen-1-yl)-cyclohexyl]-benzonitrile,
(trans)-1-[8-Chloro-1-(4-phenyl-cyclohexyl)-4H,6H-2,3,5,10b-tetraaza-benzoazulen-5-yl]-ethanone,
(trans)-8-Chloro-5-methanesulfonyl-1-(4-phenyl-cyclohexyl)-5,6-dihydro-4H-2,3,5,10b-tetraaza-benzoazulene,
(trans)-8-Chloro-5-isopropyl-1-(4-phenyl-cyclohexyl)-5,6-dihydro-4H-2,3,5,10b-tetraaza-benzoazulene,
(trans)-8-Chloro-1-(4-phenyl-cyclohexyl)-5-pyridin-2-ylmethyl-5,6-dihydro-4H-2,3,5,10b-tetraaza-benzoazulene,
(trans)-2-[8-Chloro-1-(4-phenyl-cyclohexyl)-4H,6H-2,3,5,10b-tetraaza-benzoazulen-5-yl]-ethanol, and
(trans)-8-Chloro-1-(4-phenyl-cyclohexyl)-5-pyridin-2-yl-5,6-dihydro-4H-2,3,5,10b-tetraaza-benzoazulene,
or a pharmaceutically acceptable salt thereof.

More particular compounds are
(trans)-8-Chloro-1-(4-phenyl-cyclohexyl)-5,6-dihydro-4H-2,3,5,10b-tetraaza-benzo[e]azulene hydrochloride,
(trans)-8-Chloro-5-methyl-1-(4-phenyl-cyclohexyl)-5,6-dihydro-4H-2,3,5,10b-tetraaza-benzo[e]azulene,
(trans)-8-Chloro-5-methyl-1-(4-naphthalen-1-yl-cyclohexyl)-5,6-dihydro-4H-2,3,5,10b-tetraaza-benzo[e]azulene,
(trans)-1-[8-Chloro-1-(4-phenyl-cyclohexyl)-4H,6H-2,3,5,10b-tetraaza-benzoazulen-5-yl]-ethanone,
(trans)-8-Chloro-5-isopropyl-1-(4-phenyl-cyclohexyl)-5,6-dihydro-4H-2,3,5,10b-tetraaza-benzoazulene,
(trans)-8-Chloro-1-(4-phenyl-cyclohexyl)-5-pyridin-2-ylmethyl-5,6-dihydro-4H-2,3,5,10b-tetraaza-benzoazulene, and
(trans)-2-[8-Chloro-1-(4-phenyl-cyclohexyl)-4H,6H-2,3,5,10b-tetraaza-benzoazulen-5-yl]-ethanol.

A certain embodiment of the invention is a compound as described in any of the embodiments obtainable by a process according as described herewithin.

A certain embodiment of the invention is a compound as described in any of the embodiments, whenever obtained by a process according as described herewithin.

A certain embodiment of the invention is a compound as described in any of the embodiments for the use as therapeutically active substance.

A certain embodiment of the invention is a compound as described in any of the embodiments for a use in the prevention or treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

A certain embodiment of the invention is a pharmaceutical composition comprising a compound as described in any of the embodiments.

A certain embodiment of the invention is a pharmaceutical composition comprising a compound as described in any of the embodiments, wherein it is useful for the prevention or treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

A certain embodiment of the invention is the use of a compound as described in any of the embodiments for the preparation of a medicament.

A certain embodiment of the invention is the use of a compound as described in any of the embodiments for the preparation of a medicament, wherein the medicament is useful for the prevention or treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

A certain embodiment of the invention is the use of a compound as described in any of the embodiments for the prevention or treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

A certain embodiment of the invention is a method for the therapeutic and/or prophylactic treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior, which method comprises administering a compound as defined in any if the embodiments to a human being or animal.

In a certain embodiment, the compounds of formula I of the invention can be manufactured according to a process comprising the step of reacting a compound of formula II

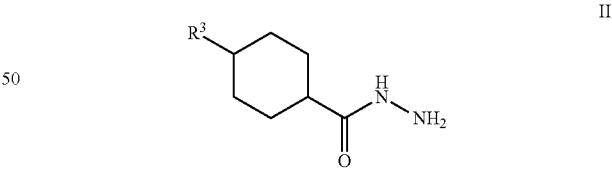

with a compound of formula III

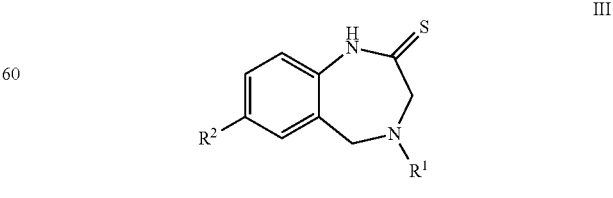

to obtain a compound of formula I wherein $R^1$, $R^2$ and $R^3$ are as defined hereinabove for formula I.

The processes are described in more detail with the following general schemes and procedures A to G.

Scheme 1: General Scheme A

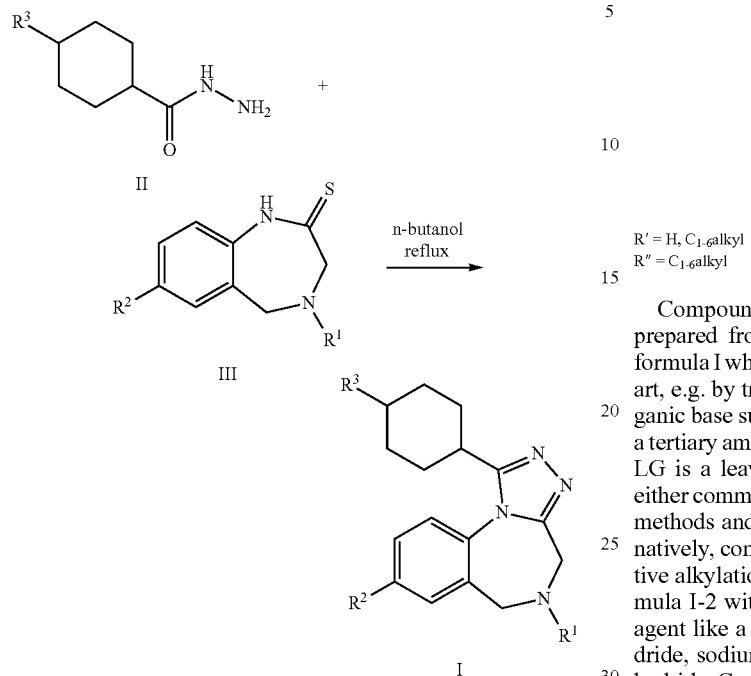

Compounds of formula I can be prepared by thermal condensation of a hydrazide of formula II and a thiolactam of formula III. The synthesis of compounds of formula II is outlined in general schemes D-G hereinafter. Compounds of formula III can be prepared following the procedures described in general scheme C as described hereinafter. General scheme A is hereinafter further illustrated with general procedure VII.

Scheme 2: General Scheme B

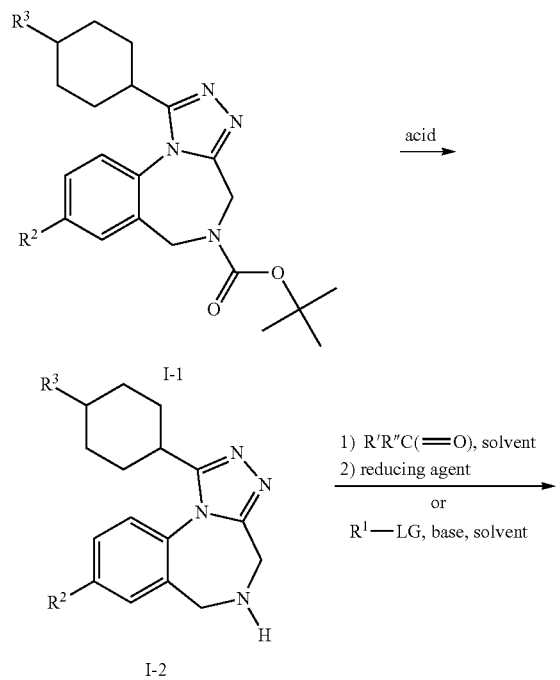

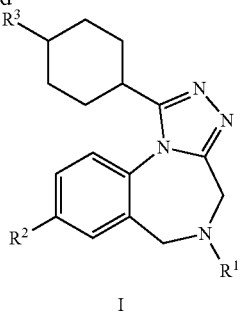

R' = H, $C_{1-6}$alkyl
R'' = $C_{1-6}$alkyl

Compounds of formula I with $R^1$ different from H can be prepared from compounds of formula I-2 (compounds of formula I wherein $R^1$ is H) according to methods known in the art, e.g. by treating a compound of formula I-2 with an inorganic base such as a carbonate salt or an organic base such as a tertiary amine and an electrophilic reactant $R^1$-LG (wherein LG is a leaving group like. halogen or sulfonyl) which is either commercially available or easily prepared according to methods and starting materials well known in the art. Alternatively, compounds of formula I can be obtained via reductive alkylation by consecutively treating a compound of formula I-2 with a ketone or aldehyde and a suitable reducing agent like a borohydride derivative such as sodium borohydride, sodium cyanoborohydride or sodium triacetoxyborohydride. Compounds of formula I-2 can be obtained by cleavage of the substituent $R^1$ of a compound of formula I using methods known in the art. Compounds of formula I-2 are conveniently obtained as the salt or the free base after basic aqueous work-up by treatment of compounds of formula I-1 (compounds of formula I in which $R^1$ is tert-butoxycarbonyl) with an acid in a suitable solvent like methanesulphonic acid in dichloromethane or tetrahydrofuran or hydrochloric acid in methanol. General scheme B is hereinafter further illustrated with general procedures VIII and IX.

Scheme 3: General Scheme C

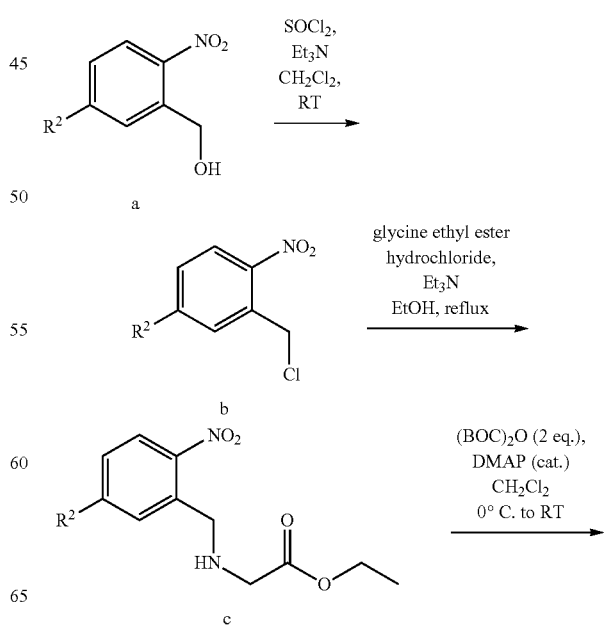

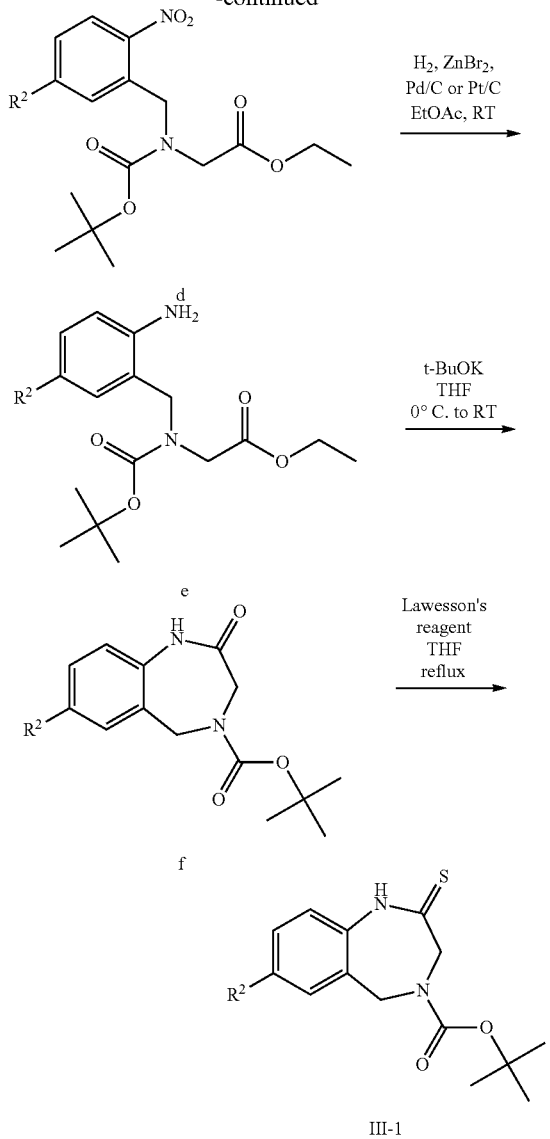

A thiolactam of formula III-1 (compounds of formula III in which R[1] is tert-butoxycarbonyl) can be obtained as follows: Transformation of a 2-nitrobenzyl alcohol of formula a to a benzylic chloride of formula b can be affected by a chlorinating reagent such as thionyl chloride in the presence of an organic tertiary amine base. Alkylation of a compound of formula b with glycine ethyl ester hydrochloride in the presence of an organic tertiary amine base and N-protection of the resulting compound of formula c using di-tert-butyl dicarbonate and a catalytic amount of 4-N,N-dimethylaminopyridine gives compounds of formula d. The nitro group can be reduced selectively by hydrogenation over palladium or platinum on charcoal, which has been pretreated with a zinc halide such as zinc bromide, to give aniline intermediates of formula e. Cyclization to lactams of formula f is achieved by treatment of compounds of formula e with a suitable base, e.g. potassium tert-butoxide, in tetrahydrofuran. A thiolactam of formula III-1 is obtained by treatment of a compound of formula f with Lawesson's reagent or phosphorous pentasulphide at elevated temperature.

Scheme 4: General Scheme D

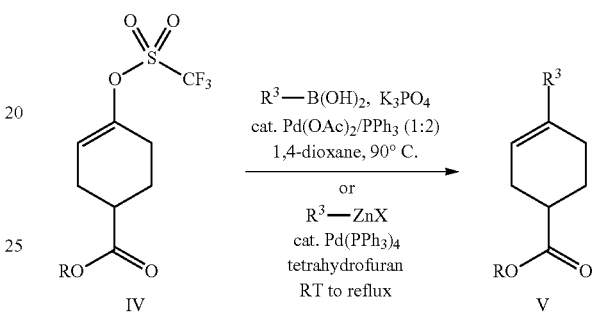

R = Me, Et
X = halogen

4-Aryl-cyclohex-3-enyl carboxylic acid ester intermediates of formula V can be prepared under the conditions of the Suzuki reaction from a 4-trifluoromethanesulfonyloxy-cyclohex-3-enecarboxylic acid ester of formula IV and an aryl boronic acid, an aryl boronic acid ester or an aryl trifluoroborate salt in a suitable organic solvent such as 1,4-dioxane, tetrahydrofuran or toluene in the presence of catalytic amounts of a 1:2 mixture of palladium(II) acetate and triphenylphosphine or a 1:1 mixture of palladium(II) acetate and a bisphosphine ligand or tetrakis(triphenylphosphine)palladium(0) and in the presence of a base such as potassium phosphate or potassium carbonate, which is used neat or as an aqueous solution, at a reaction temperature between room temperature and reflux. Alternatively 4-aryl-cyclohex-3-enyl carboxylic acid ester intermediates of formula V can be prepared under the conditions of the Negishi reaction from a 4-trifluoromethanesulfonyloxy-cyclohex-3-enecarboxylic acid ester of formula IV and an aryl zinc halide in a suitable organic solvent such as tetrahydrofuran and Pd(PPh)$_3$ at a reaction temperature between room temperature and reflux. General scheme D is hereinafter further illustrated with general procedure I.

Scheme 5: General Scheme E

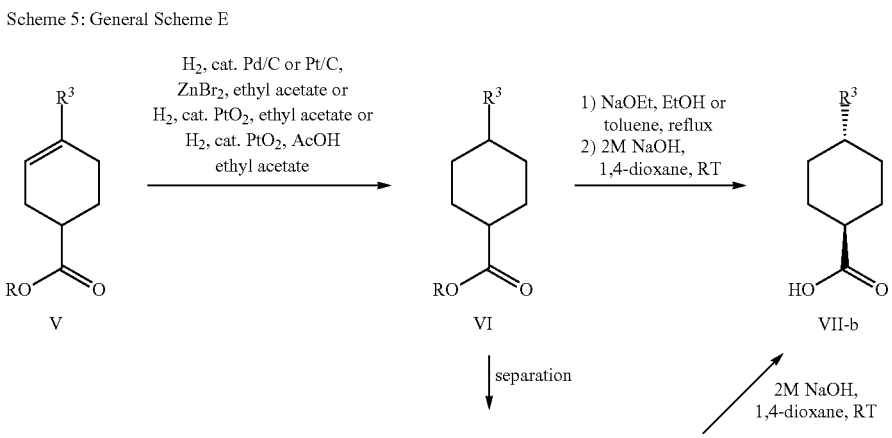

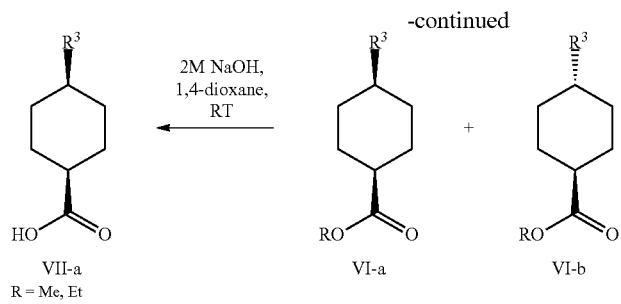

VII-a
R = Me, Et

4-Aryl-cyclohexane carboxylic acid ester intermediates of formula VI are usually obtained as a mixture of the cis and the trans isomer by reduction of 4-aryl-cyclohex-3-enyl carboxylic acid ester intermediates of formula V under an atmosphere of hydrogen gas (1 bar) in a suitable solvent such as ethyl acetate or an alcohol in the presence of a catalytic amount of palladium or platinum on charcoal or platinum(IV) oxide at room temperature. The addition of one equivalent of acetic acid can be beneficial in some cases. Pretreatment of the palladium or platinum catalyst with a zinc halide can prevent or reduce dehalogenation of compounds of formula V and VI, the residue $R^3$ of which is substituted with one or more halide substituents other than fluorine. Cis/trans mixtures of 4-aryl-cyclohexane carboxylic acid ester intermediates of formula VI can in some cases be separable by the usual methods such as silica gel column or high performance chromatography or crystallization into pure cis-4-aryl-cyclohexane carboxylic acid ester intermediates of formula VI-a and trans-4-aryl-cyclohexane carboxylic acid ester intermediates of formula VI-b, which can be saponified to pure cis-4-aryl-cyclohexane carboxylic acid intermediates of formula VII-a and trans-4-aryl-cyclohexane carboxylic acid intermediates of formula VII-b under standard conditions such as stirring in a mixture of aqueous sodium hydroxide solution and an etheral solvent such as 1,4-dioxane, tetrahydrofuran or diethyl ether a room temperature. Alternatively, trans-4-aryl-cyclohexane carboxylic acid intermediates of formula VII-b can be obtained by epimerization of the cis isomer of cis/trans-mixtures of 4-aryl-cyclohexane carboxylic acid ester intermediates of formula VI using a suitable base, e.g. an alkali metal alkoxide such as sodium or potassium ethylate, in a suitable solvent such as ethanol or toluene at reflux followed by saponification of the crude reaction mixture under standard conditions such as stirring in a mixture of aqueous sodium hydroxide solution and an etheral solvent such as 1,4-dioxane, tetrahydrofuran or diethyl ether a room temperature. General scheme E is hereinafter further illustrated with general procedures II, III and IV.

Scheme 6: General Scheme F

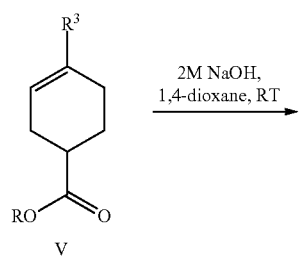

V

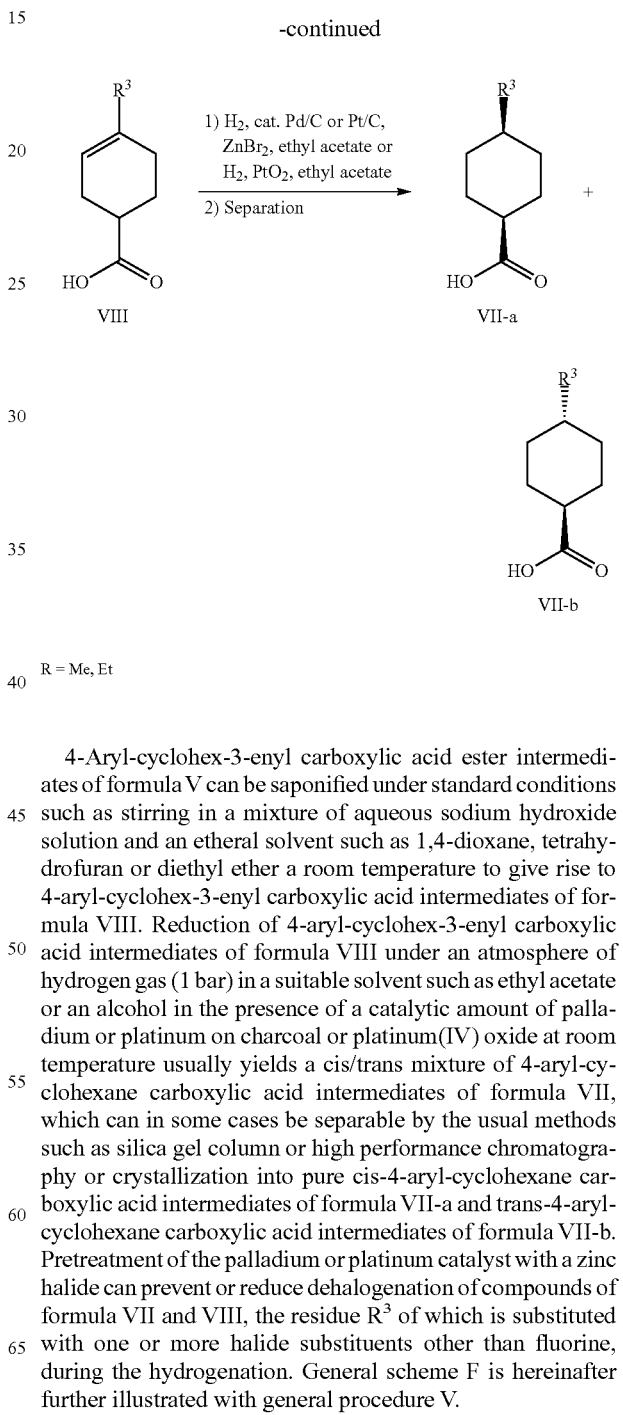

R = Me, Et

4-Aryl-cyclohex-3-enyl carboxylic acid ester intermediates of formula V can be saponified under standard conditions such as stirring in a mixture of aqueous sodium hydroxide solution and an etheral solvent such as 1,4-dioxane, tetrahydrofuran or diethyl ether a room temperature to give rise to 4-aryl-cyclohex-3-enyl carboxylic acid intermediates of formula VIII. Reduction of 4-aryl-cyclohex-3-enyl carboxylic acid intermediates of formula VIII under an atmosphere of hydrogen gas (1 bar) in a suitable solvent such as ethyl acetate or an alcohol in the presence of a catalytic amount of palladium or platinum on charcoal or platinum(IV) oxide at room temperature usually yields a cis/trans mixture of 4-aryl-cyclohexane carboxylic acid intermediates of formula VII, which can in some cases be separable by the usual methods such as silica gel column or high performance chromatography or crystallization into pure cis-4-aryl-cyclohexane carboxylic acid intermediates of formula VII-a and trans-4-aryl-cyclohexane carboxylic acid intermediates of formula VII-b. Pretreatment of the palladium or platinum catalyst with a zinc halide can prevent or reduce dehalogenation of compounds of formula VII and VIII, the residue $R^3$ of which is substituted with one or more halide substituents other than fluorine, during the hydrogenation. General scheme F is hereinafter further illustrated with general procedure V.

Scheme 7: General Scheme G

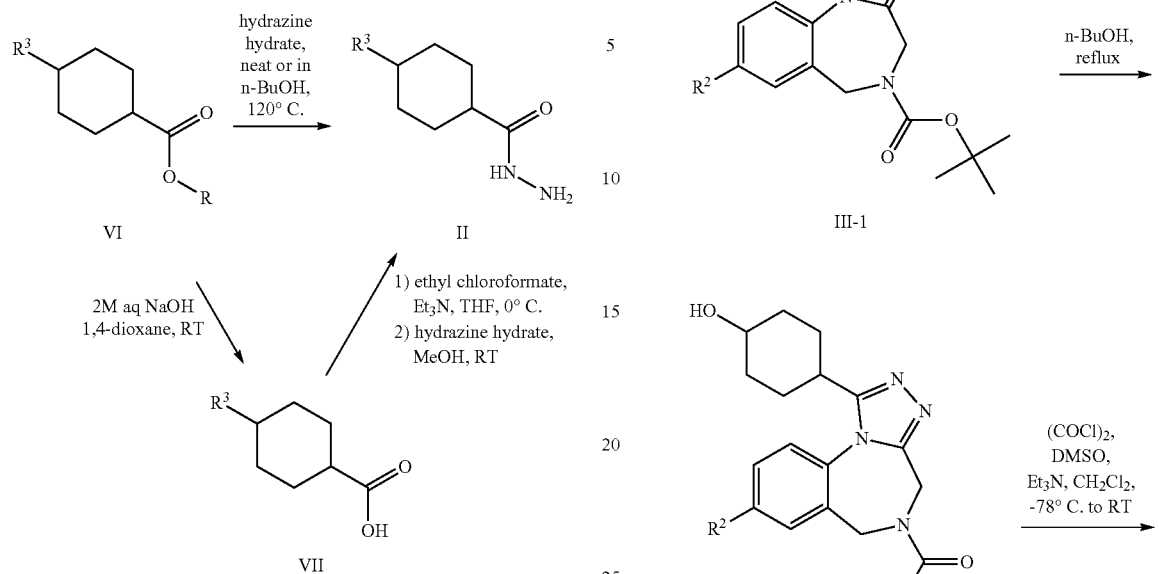

R = Me, Et

A 4-aryl-cyclohexanecarboxylic acid ester intermediate of formula VI can be converted to a hydrazide of formula II by heating with hydrazine hydrate. Alternatively, an ester of formula VI can be hydrolyzed to a carboxylic acid of formula VII using a biphasic mixture of aqueous sodium or potassium hydroxide solution and an etheral solvent such as dioxane, tetrahydrofuran or diethyl ether. A hydrazide of formula II can be obtained by activating an acid intermediate of formula VII, e.g. with ethyl chloroformate, thionyl chloride, oxalyl-chloride or a peptide coupling reagent, and subsequent coupling with hydrazine. General scheme G is hereinafter further illustrated with general procedure VI.

In a certain embodiment, compounds of formulas I-a and I-b can be manufactured according to the procedures described hereinafter in general scheme H.

Scheme 8: General Scheme H

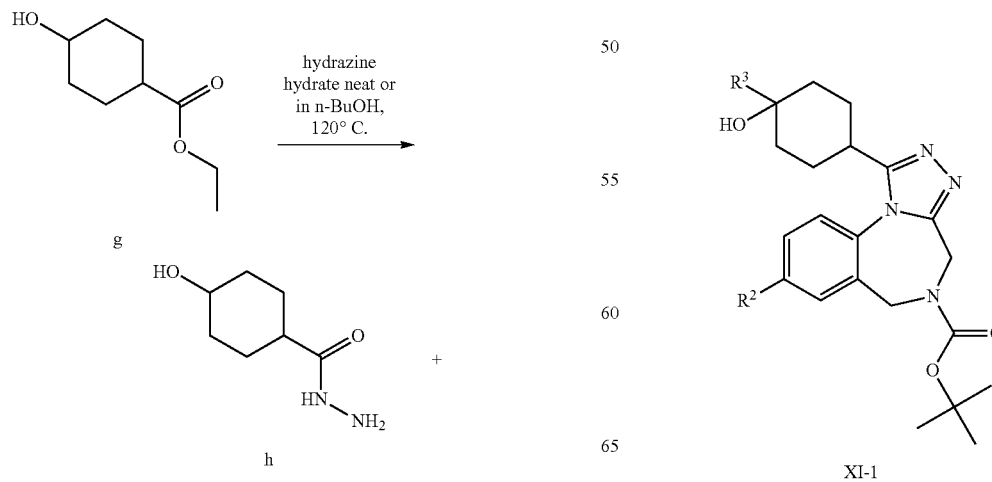

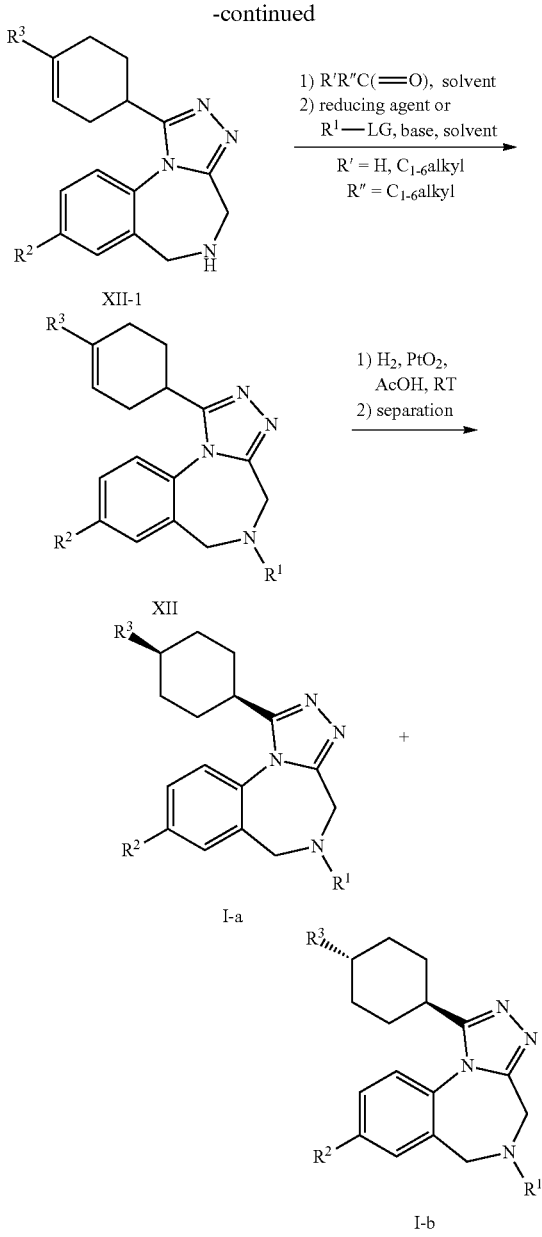

4-Hydroxy-cyclohexanecarboxylic acid ethyl ester g can be converted to 4-hydroxy-cyclohexanecarboxylic acid hydrazide h by heating with hydrazine hydrate. Thermal condensation of 4-hydroxy-cyclohexanecarboxylic acid hydrazide h with a thiolactam of formula III-1 gives rise to a triazole of formula IX-1, which can be oxidized to a ketone of formula X-1 under conditions known in the art such as the Swern reaction. A tertiary alcohol of formula XI-1 can be prepared by addition of a Grignard reagent of formula i to the carbonyl group of a compound of formula X-1. Treatment of a compound of formula XI-1 with an acid in a suitable solvent, e.g. methanesulphonic acid in dichloromethane or tetrahydrofuran or hydrochloric acid in methanol, leads to a compound of formula XII-1 as the salt or the free base after basic aqueous work-up. Compounds of formula XII with $R^1$ different from H can be prepared from compounds of formula XII-1 (compounds of formula XII wherein $R^1$ is H) according to methods known in the art, e.g. by treating a compound of formula XII-1 with an inorganic base such as a carbonate salt or an organic base such as a tertiary amine and an electrophilic reactant $R^1$-LG (wherein LG is a leaving group, e.g. halogen or sulfonyl) which is either commercially available or easily prepared according to methods and starting materials well known in the art. Alternatively, compounds of formula XII can be obtained via reductive alkylation by consecutively treating a compound of formula XII-1 with a ketone or aldehyde and a suitable reducing agent, e.g. a borohydride such as sodium borohydride, sodium cyanoborohydride or sodium triacetoxyborohydride. Reduction of compounds of formula XII under an atmosphere of hydrogen gas (1 bar) in a suitable solvent such as ethyl acetate or an alcohol in the presence of a catalytic amount of palladium or platinum on charcoal or platinum(IV) oxide at room temperature usually leads to a cis/trans mixture of compounds of formula I. Under these reaction conditions compounds of formula I in which $R^2$ is chlorine or bromine can be partially or completely dehalogenated to compounds of formula I in which $R^2$ is hydrogen. Dehalogenation can be reduced or prevented by pretreatment of the palladium or platinum catalyst with a zinc halide. The addition of one equivalent of acetic acid can be beneficial in some cases. Cis/trans mixtures of compounds of formula I can in some cases be separable into pure cis isomers of formula I-a and trans isomers of formula I-b by the usual methods such as silica gel column or high performance chromatography or crystallization.

The corresponding pharmaceutically acceptable salts with acids can be obtained by standard methods known to the person skilled in the art, e.g. by dissolving the compound of formula I in a suitable solvent such as e.g. dioxan or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M is a metal or ammonium cation and n is the number of hydroxide anions, to a solution of the compound in a suitable solvent (e.g. ethanol, ethanol-water mixture, tetrahydrofuran-water mixture) and to remove the solvent by evaporation or lyophilisation.

Insofar as their preparation is not described in the examples, the compounds of formula I as well as all intermediate products can be prepared according to analogous methods or according to the methods set forth herewithin. Starting materials are commercially available, known in the art or can be prepared by methods known in the art or in analogy thereto.

It will be appreciated that the compounds of formula I in this invention can be derivatised at functional groups to provide derivatives which are capable of conversion back to the parent compound in vivo.

Pharmacological Tests

The compounds of the present invention exhibit V1a activity. They are selective inhibitors of the V1a receptor and are therefore likely to have a low potential to cause unwanted off-target related side-effects. The V1a activity can be detected as described below.

The human V1a receptor was cloned by RT-PCR from total human liver RNA. The coding sequence was subcloned in an expression vector after sequencing to confirm the identity of the amplified sequence. To demonstrate the affinity of the compounds from the present invention to the human V1a receptor binding studies were performed. Cell membranes were prepared from HEK293 cells transiently transfected with the expression vector and grown in 20 liter fermenters with the following protocol.

50 g of cells are resuspended in 30 ml freshly prepared ice cold Lysis buffer (50 mM HEPES, 1 mM EDTA, 10 mM magnesium dichloride adjusted to pH=7.4+complete cocktail of protease inhibitor (Roche Diagnostics)). Homogenized with Polytron for 1 min and sonicated on ice for 2×2 minutes at 80% intensity (Vibracell sonicator). The preparation is centrifuged 20 min at 500 g at 4° C., the pellet is discarded and the supernatant centrifuged 1 hour at 43,000 g at 4° C. (19,000 rpm). The pellet is resuspended in 12.5 ml Lysis buffer+12.5 ml sucrose 20% and homogenized using a Polytron for 1-2 min. The protein concentration is determined by the Bradford method and aliquots are stored at −80° C. until use. For binding studies 60 mg Yttrium silicate SPA beads (Amersham®) are mixed with an aliquot of membrane in binding buffer (50 mM Tris, 120 mM sodium chloride, 5 mM potassium chloride, 2 mM calcium dichloride, 10 mM magnesium dichloride) for 15 minutes with mixing. 50 µl of bead/membrane mixture is then added to each well of a 96 well plate, followed by 50 µl of 4 nM 3H-Vasopressin (American Radiolabeled Chemicals). For total binding measurement 100 µl of binding buffer are added to the respective wells, for non-specific binding 100 µl of 8.4 mM cold vasopressin and for compound testing 100 µl of a serial dilution of each compound in 2% dimethyl sulfoxide. The plate is incubated 1 h at room temperature, centrifuged 1 min at 1000 g and counted on a Packard Top-Count. Non-specific binding counts are subtracted from each well and data is normalized to the maximum specific binding set at 100%. To calculate an $IC_{50}$ the curve is fitted using a non-linear regression model (XLfit) and the Ki is calculated using the Cheng-Prussoff equation.

The following representative data show the antagonistic activity against human V1a receptor of compounds according to present invention.

TABLE 2

| human V1a pKi of selected examples | |
|---|---|
| Ex# | pKi (hV1a) |
| 1 | 8.19 |
| 2 | 8.68 |
| 3 | 9.10 |
| 4 | 7.79 |
| 5 | 8.37 |
| 6 | 6.47 |
| 7 | 7.28 |
| 8 | 6.52 |
| 9 | 7.52 |
| 10 | 8.33 |
| 11 | 8.20 |
| 12 | 8.66 |
| 13 | 7.74 |
| 14 | 7.24 |
| 15 | 7.99 |
| 16 | 8.38 |
| 17 | 7.82 |
| 18 | 8.51 |
| 19 | 8.22 |
| 20 | 7.69 |
| 21 | 8.12 |
| 22 | 7.95 |
| 23 | 7.37 |
| 24 | 8.24 |
| 25 | 8.15 |
| 26 | 7.49 |
| 27 | 8.57 |
| 28 | 8.89 |
| 29 | 8.74 |

TABLE 2-continued

| human V1a pKi of selected examples | |
|---|---|
| Ex# | pKi (hV1a) |
| 30 | 8.72 |
| 31 | 8.62 |
| 32 | 8.85 |
| 33 | 8.05 |

Pharmaceutical Compositions

The present invention provides pharmaceutical compositions comprising compounds of formula I as well as their pharmaceutically acceptable salts and a pharmaceutically acceptable carrier. Such pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and their pharmaceutically acceptable salts can be processed with pharmaceutically inert, inorganic or organic excipients for the production of tablets, coated tablets, dragées and hard gelatin capsules. Lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semisolid and liquid polyols etc.

Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 10 to 1000 mg per person of a compound of formula I should be appropriate, although the above upper limit can also be exceeded when necessary.

Examples of compositions according to the invention are, but are not limited to:

Example A

Tablets of the following composition are manufactured in the usual manner:

TABLE 3

| possible tablet composition | | | | |
|---|---|---|---|---|
| | mg/tablet | | | |
| ingredient | | | | |
| 1. compound of formula I | 5 | 25 | 100 | 500 |
| 2. lactose | 45 | 105 | 30 | 150 |
| 3. corn starch | 15 | 6 | 6 | 60 |

TABLE 3-continued possible tablet composition

| ingredient | mg/tablet | | | |
|---|---|---|---|---|
| | 5 | 25 | 100 | 500 |
| 4. microcrystalline cellulose | 34 | 30 | 30 | 450 |
| 5. magnesium stearate | 1 | 1 | 1 | 1 |
| total | 100 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 4 possible capsule ingredient composition

| ingredient | mg/capsule | | | | |
|---|---|---|---|---|---|
| | 5 | 10 | 25 | 100 | 500 |
| 1. compound of formula I | 5 | 10 | 25 | 100 | 500 |
| 2. lactose | 159 | 155 | 123 | 148 | — |
| 3. corn starch | 25 | 30 | 35 | 40 | 70 |
| 4. talc | 10 | 5 | 15 | 10 | 25 |
| 5. magnesium stearate | 1 | — | 2 | 2 | 5 |
| total | 200 | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer, the talc (and magnesium stearate) is added thereto and mixed thoroughly. The mixture is filled by machine into suitable capsules, e.g. hard gelatin capsules.

Example B-2

Soft Gelatin Capsules of the following composition are manufactured:

TABLE 5 possible soft gelatin capsule ingredient composition

| ingredient | mg/capsule |
|---|---|
| compound of formula I | 5 |
| yellow wax | 8 |
| hydrogenated soybean oil | 8 |
| partially hydrogenated plant oils | 34 |
| soybean oil | 110 |
| total | 165 |

TABLE 6 possible soft gelatin capsule composition

| ingredient | mg/capsule |
|---|---|
| gelatin | 75 |
| glycerol 85% | 32 |
| karion 83 | 8 (dry matter) |
| titan dioxide | 0.4 |
| iron oxide yellow | 1.1 |
| total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 7 possible suppository composition

| ingredient | mg/supp. |
|---|---|
| compound of formula I | 15 |
| suppository mass | 1285 |
| total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 8 possible injection solution composition

| ingredient | mg/injection solution. |
|---|---|
| compound of formula I | 3 |
| polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 9

| possible sachet composition | |
|---|---|
| ingredient | mg/sachet |
| compound of formula I | 50 |
| lactose, fine powder | 1015 |
| microcrystalline cellulose (AVICEL PH 102) | 1400 |
| sodium carboxymethyl cellulose | 14 |
| polyvinylpyrrolidon K 30 | 10 |
| Magnesium stearate | 10 |
| flavoring additives | 1 |
| total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

EXAMPLES

The following examples are provided for illustration of the invention. They should not be considered as limiting the scope of the invention, but merely as being representative thereof.

Intermediate of Formula IV (RS)-4-Trifluoromethanesulfonyloxy-cyclohex-3-enecarboxylic acid ethyl ester

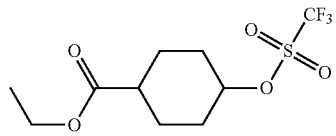 [SMILES: CCOC(=O)C1CCC(OS(=O)(=O)C(F)(F)F)CC1]

To a solution of ethyl-4-cyclohexanonecarboxylate (25.0 g, 147 mmol) in tetrahydrofuran (580 ml) was added a 1M solution of lithium bis(trimethylsilyl)amid in tetrahydrofuran (154 ml, 154 mmol) at −78° C. Stirring for 1 h was followed by addition of a solution of N-phenyl-bis(trifluoromethanesulfonimide) (55.1 g, 154 mmol) in tetrahydrofuran (80 ml). The cooling bath was removed 30 minutes after completed addition, and the reaction mixture was stirred for 12 h at room temperature. The mixture was quenched with 1 M aqueous sodium hydrogen sulfate solution (154 ml, 154 mmol). The solvent was removed by rotary evaporation (water bath of 40° C.). The residue was partitioned between tert-butyl methyl ether (500 ml) and 0.5 M aqueous sodium hydroxide solution (400 ml). The organic layer was washed with two 400-ml portions of 0.5 M aqueous sodium hydroxide solution, one 200-ml portion of saturated ammonium chloride solution and one 100-ml portion of brine, dried over anhydrous sodium sulfate and concentrated in vacuo to give the title compound (41.8 g, 94.2%) as yellow oil, which was used in the following steps without further purification. MS m/e: 273 ([M−$C_2H_5$]$^-$).

4-Aryl-cyclohex-3-enecarboxylic acid ester intermediates of formula V

General Procedure (I): Suzuki Coupling

To mixture of (RS)-4-trifluoromethanesulfonyloxy-cyclohex-3-enecarboxylic acid ethyl ester (1 eq), an aryl boronic acid (1.5 eq) and potassium phosphate (2 eq) in 1,4-dioxane (0.3 M), which has been purged with argon, are consecutively added triphenylphosphine (0.1 eq) and palladium(II) acetate (0.05 eq). The mixture is stirred at reflux for 20 h. After cooling to room temperature the solids are removed by filtration over Decalite®. The filtrate is concentrated in vacuo. Purification by flash-chromatography gives a 4-aryl-cyclohex-3-enecarboxylic acid ester intermediate of formula V.

4-Aryl-cyclohex-3-enecarboxylic acid ester 1 (RS)-4-Phenyl-cyclohex-3-enecarboxylic acid ethyl ester

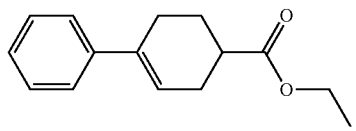

The title compound was obtained as colorless oil in 59% yield from phenylboronic acid according to general procedure (I). MS m/e: 230 (M$^+$)

4-Aryl-cyclohex-3-enecarboxylic acid ester 2 (RS)-4-(4-Fluoro-phenyl)-cyclohex-3-enecarboxylic acid ethyl ester

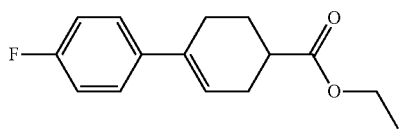 [SMILES: CCOC(=O)C1CC=C(c2ccc(F)cc2)CC1]

The title compound was obtained as colorless oil in 63% yield from 4-fluorophenylboronic acid according to general procedure (I). MS m/e: 248 (M$^+$)

4-Aryl-cyclohex-3-enecarboxylic acid ester 3 (RS)-4-(3-Trifluoromethoxy-phenyl)-cyclohex-3-enecarboxylic acid ethyl ester

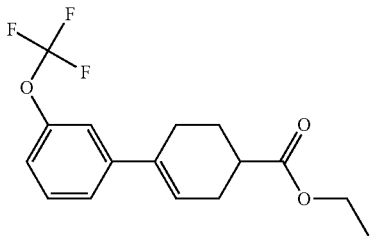 [SMILES: CCOC(=O)C1CC=C(c2cccc(OC(F)(F)F)c2)CC1]

The title compound was obtained as light yellow oil in 70% yield from 3-trifluoromethoxy)phenylboronic acid according to general procedure (I). MS m/e: 315 (M$^+$)

4-Aryl-cyclohex-3-enecarboxylic acid ester 4 (RS)-4-(2-Chloro-3-fluoro-phenyl)-cyclohex-3-enecarboxylic acid ethyl ester

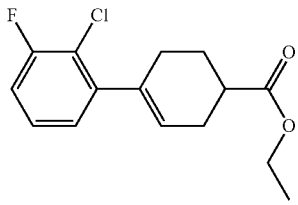 [SMILES: CCOC(=O)C1CC=C(c2cccc(F)c2Cl)CC1]

The title compound was obtained as light yellow oil in 74% yield from (2-chloro-3-fluorophenyl)boronic acid according to general procedure (I). MS m/e: 283 (M+H$^+$)

4-Aryl-cyclohex-3-enecarboxylic acid ester 5 (RS)-4-Naphthalen-1-yl-cyclohex-3-enecarboxylic acid ethyl ester

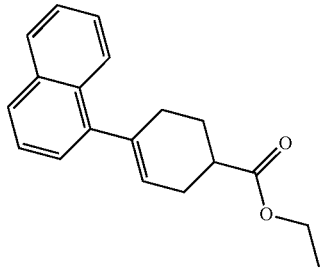 [SMILES: CCOC(=O)C1CC=C(c2cccc3ccccc23)CC1]

The title compound was obtained as light yellow oil in 68% yield from 1-naphtylboronic acid according to general procedure (I). MS m/e: 280 (M$^+$)

4-Aryl-cyclohex-3-enecarboxylic acid ester 6 (RS)-4-(5-Fluoro-2-methoxy-phenyl)-cyclohex-3-enecarboxylic acid ethyl ester

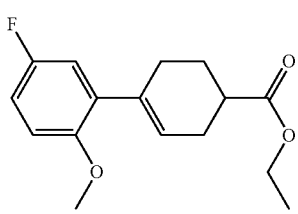 [SMILES: CCOC(=O)C1CC=C(c2cc(F)ccc2OC)CC1]

The title compound was obtained as light yellow liquid in 62% yield from 5-fluoro-2-methoxyphenylboronic acid according to general procedure (I). MS m/e: 279 (M+H$^+$)

4-Aryl-cyclohex-3-enecarboxylic acid ester 7 (RS)-4-(3-Cyano-phenyl)-cyclohex-3-enecarboxylic acid ethyl ester

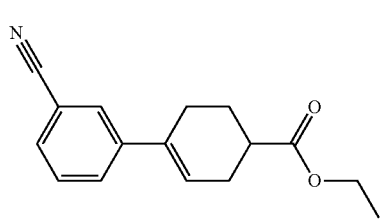 [SMILES: CCOC(=O)C1CC=C(c2cccc(C#N)c2)CC1]

The title compound was obtained as colorless oil in 53% yield from 3-cyanophenylboronic acid according to general procedure (I). MS m/e: 256 (M+H$^+$)

4-Aryl-cyclohexanecarboxylic acid ester intermediates of formula VI

General Procedure (II): Platinum(IV) Oxide Catalyzed Hydrogenation

A solution of a 4-aryl-cyclohex-3-enecarboxylic acid ester intermediate of formula V in ethyl acetate (0.1 M) and optionally an additive such as acetic acid (1 eq) is purged with argon. Addition of platinum(IV)oxide (0.3 eq) is followed by filling the flask with hydrogen. The reaction mixture is stirred at room temperature under an atmosphere of hydrogen (1 bar) for 1-16 h. The catalyst is removed by filtration over Decalite®. The filtrate is concentrated to dryness to give a cis/trans mixture of a crude 4-aryl-cyclohexanecarboxylic acid ester intermediate of formula VI, which can usually be used in the next step without further purification.

General Procedure (III): Palladium on Charcoal Catalyzed Hydrogenation

A solution of a 4-aryl-cyclohex-3-enecarboxylic acid ester intermediate of formula V and zinc bromide (0.2 eq) in ethyl acetate (0.1 M) is purged with argon. Addition of 10% palladium on activated charcoal (0.05 eq) is followed by filling the flask with hydrogen. The reaction mixture is stirred at room temperature under an atmosphere of hydrogen (1 bar) for 20-72 h. The catalyst is removed by filtration over Decalite®. The filtrate is washed with one portion of water. The aqueous layer is extracted with one or two portions of ethyl acetate. The combined organic layers are dried over anhydrous sodium sulfate and concentrated to dryness to give a cis/trans mixture of a crude 4-aryl-cyclohexanecarboxylic acid ester intermediate of formula VI, which can usually be used in the next step without further purification.

4-Aryl-cyclohexanecarboxylic acid ester intermediate 1
cis/trans-4-Phenyl-cyclohexanecarboxylic acid ethyl ester (2:1)

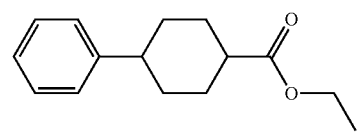 [SMILES: CCOC(=O)C1CCC(c2ccccc2)CC1]

The title compound was obtained as colorless oil in 98% yield from (RS)-4-phenyl-cyclohex-3-enecarboxylic acid ethyl ester according to general procedure (III). MS m/e: 232 (M$^+$)

cis/trans-4-(4-Fluoro-phenyl)-cyclohexanecarboxylic acid ethyl ester (3:1)

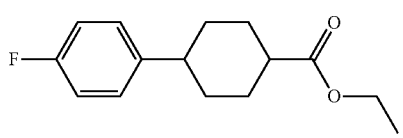

The title compound was obtained as light brown oil in quantitative yield from (RS)-4-(4-fluoro-phenyl)-cyclohex- 3-enecarboxylic acid ethyl ester according to general procedure (III). MS m/e: 250 (M⁺)

cis/trans-4-(3-Trifluoromethoxy-phenyl)-cyclohexanecarboxylic acid ethyl ester (7:3)

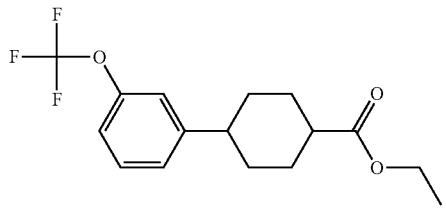 [SMILES: CCOC(=O)C1CCC(c2cccc(OC(F)(F)F)c2)CC1]

The title compound was obtained as light yellow oil in 93% yield from (RS)-4-(3-trifluoromethoxy-phenyl)-cyclohex-3-enecarboxylic acid ethyl ester according to general procedure (III). MS m/e: 316 (M⁺)

cis/trans-4-(2-Chloro-3-fluoro-phenyl)-cyclohexanecarboxylic acid ethyl ester (7:3)

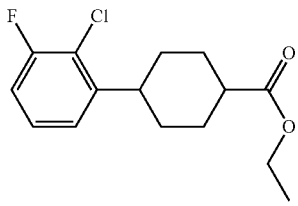 [SMILES: CCOC(=O)C1CCC(c2cccc(F)c2Cl)CC1]

The title compound was obtained as light yellow oil in 94% yield from (RS)-4-(2-chloro-3-fluoro-phenyl)-cyclohex-3-enecarboxylic acid ethyl ester according to general procedure (II). MS m/e: 284 (M+H⁺)

4-Naphthalen-1-yl-cyclohexanecarboxylic acid ethyl ester

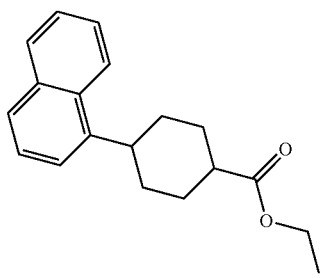 [SMILES: CCOC(=O)C1CCC(c2cccc3ccccc23)CC1]

The title compound was obtained as off-white solid in 91% yield from (RS)-4-naphthalen-1-yl-cyclohex-3-enecarboxylic acid ethyl ester according to general procedure (II) using acetic acid (1 eq) as additive. MS m/e: 282 (M⁺)

4-(5-Fluoro-2-methoxy-phenyl)-cyclohexanecarboxylic acid ethyl ester

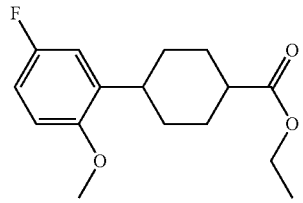 [SMILES: CCOC(=O)C1CCC(c2cc(F)ccc2OC)CC1]

The title compound was obtained as light brown oil in 90% yield from (RS)-4-(5-fluoro-2-methoxy-phenyl)-cyclohex-3-enecarboxylic acid ethyl ester according to general procedure (II). MS m/e: 280 (M⁺)

cis/trans-4-(3-Cyano-phenyl)-cyclohexanecarboxylic acid ethyl ester (3:1)

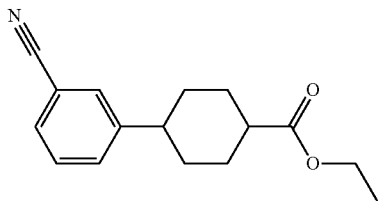 [SMILES: CCOC(=O)C1CCC(c2cccc(C#N)c2)CC1]

The title compound was obtained as colorless oil in 97% yield from (RS)-4-(3-cyano-phenyl)-cyclohex-3-enecarboxylic acid ethyl ester according to general procedure (III). MS m/e: 257 (M⁺)

4-Aryl-cyclohexanecarboxylic acid intermediates of formula VII

General procedure (IV): Epimerization of 4-aryl-cyclohexanecarboxylic acid ester Intermediates Followed by Saponification A mixture of a 4-aryl-cyclohexanecarboxylic acid ester intermediate of formula VI and a sodium alkoxide such as sodium ethylate (3-6 eq) in ethanol or toluene is heated at reflux for 20-72 h. After cooling to room temperature 2 M aqueous sodium hydroxide solution (10-20 eq) is added and the mixture is heated at reflux for 1-2 h. The reaction mixture is cooled to room temperature and partitioned between an organic solvent such as ethyl acetate or tert-butyl methyl ether and water. The layers are separated. The organic layer is extracted with one or two portions 0.5 M aqueous sodium hydroxide solution. The combined aqueous layers are acidified by addition of concentrated hydrochloric acid and extracted with two or three portions of organic solvent. The combined organic extracts are dried over anhydrous sodium sulfate and concentrated to dryness. Purification by flash-chromatography gives a trans-4-aryl-cyclohexanecarboxylic acid intermediate of formula VII-b.

General procedure (V): Saponification of 4-aryl-cyclohex-3-enecarboxylic acid ester Intermediates Followed by Hydrogenation A mixture of a 4-aryl-cyclohex-3-enecarboxylic acid ester intermediate of formula V and 2 M aqueous sodium hydroxide solution (10 eq) in 1,4-dioxane (0.1-0.2 M) is stirred at room temperature for 3-48 h. The reaction mixture is partitioned between an organic solvent such as ethyl acetate or tert-butyl methyl ether and water. The organic layer is extracted with one or two portions of 0.5 M aqueous sodium hydroxide solution. The aqueous layer is acidified by addition of concentrated hydrochloric acid and extracted with two or three portions of organic solvent. The combined organic layers are dried over anhydrous sodium sulfate and concentrated to dryness. A solution of the crude 4-aryl-cyclohex-3-enecarboxylic acid intermediate of formula VIII and zinc bromide (0.2 eq) in ethyl acetate (0.1 M) is purged with argon. Addition of 10% palladium on activated charcoal (0.05 eq) is followed by filling the flask with hydrogen. The reaction mixture is stirred at room temperature under an atmosphere of hydrogen (1 bar) for 20-72 h. The catalyst is removed by filtration over Decalite®. The filtrate is washed with one portion of water. The aqueous layer is extracted with one or two portions of ethyl acetate. The combined organic layers are dried over anhydrous sodium sulfate and concentrated to dryness. Purification by flash-chromatography gives a mixture of a cis-4-aryl-cyclohexanecarboxylic acid intermediate of formula VII-a and a trans-4-aryl-cyclohexanecarboxylic acid intermediate of formula VII-b.

4-Aryl-cyclohexanecarboxylic acid 1
trans-4-Phenyl-cyclohexanecarboxylic acid

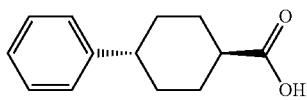 [SMILES: O=C(O)[C@H]1CC[C@H](c2ccccc2)CC1]

The title compound was obtained as white solid in 63% yield from cis/trans-4-phenyl-cyclohexanecarboxylic acid ethyl ester (2:1) according to general procedure (IV). MS m/e: 203 ([M+H]$^-$)

4-Aryl-cyclohexanecarboxylic acid 2
cis-4-(4-Fluoro-phenyl)-cyclohexanecarboxylic acid

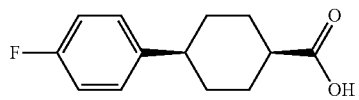 [SMILES: O=C(O)[C@H]1CC[C@@H](c2ccc(F)cc2)CC1]

and

4-Aryl-cyclohexanecarboxylic acid 3
trans-4-(4-Fluoro-phenyl)-cyclohexanecarboxylic acid

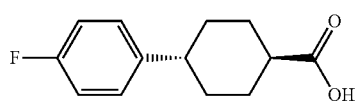 [SMILES: O=C(O)[C@H]1CC[C@H](c2ccc(F)cc2)CC1]

cis-4-(4-Fluoro-phenyl)-cyclohexanecarboxylic acid and trans-4-(4-fluoro-phenyl)-cyclohexanecarboxylic acid were obtained from (RS)-4-(4-fluoro-phenyl)-cyclohex-3-enecarboxylic acid ethyl ester according to general procedure (V) after separation by flash-column chromatography.

cis-4-(4-Fluoro-phenyl)-cyclohexanecarboxylic acid was obtained as white solid in 64% yield. MS m/e: 221 ([M–H]$^-$)

trans-4-(4-Fluoro-phenyl)-cyclohexanecarboxylic acid was obtained as white solid in 14% yield MS m/e: 221 ([M–H]$^-$)

4-Aryl-cyclohexanecarboxylic acid 4 trans-4-(3-Trifluoromethoxy-phenyl)-cyclohexanecarboxylic acid

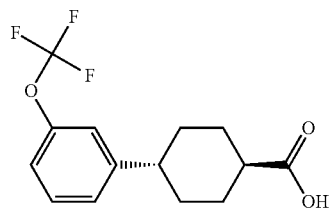 [SMILES: O=C(O)[C@H]1CC[C@H](c2cccc(OC(F)(F)F)c2)CC1]

The title compound was obtained as light yellow solid in 50% yield from cis/trans-4-(3-trifluoromethoxy-phenyl)-cyclohexanecarboxylic acid ethyl ester (7:3) according to general procedure (IV). MS m/e: 287 ([M–H]$^-$)

4-Aryl-cyclohexanecarboxylic acid 5 trans-4-(2-Chloro-3-fluoro-phenyl)-cyclohexanecarboxylic acid

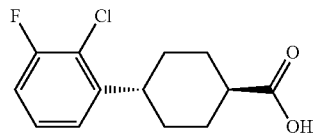 [SMILES: O=C(O)[C@H]1CC[C@H](c2cccc(F)c2Cl)CC1]

The title compound was obtained as white solid in 61% yield from cis/trans-4-(2-chloro-3-fluoro-phenyl)-cyclohexanecarboxylic acid ethyl ester (7:3) according to general procedure (IV). MS m/e: 255 ([M–H]$^-$)

4-Aryl-cyclohexanecarboxylic acid 6
trans-4-Naphthalen-1-yl-cyclohexanecarboxylic acid

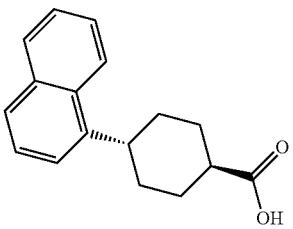 [SMILES: O=C(O)[C@H]1CC[C@H](c2cccc3ccccc32)CC1]

The title compound was obtained as off-white solid in 36% yield from 4-naphthalen-1-yl-cyclohexanecarboxylic acid ethyl ester according to general procedure (IV). MS m/e: 253 ([M–H]$^-$)

4-Aryl-cyclohexanecarboxylic acid 7 trans-4-(5-Fluoro-2-methoxy-phenyl)-cyclohexanecarboxylic acid

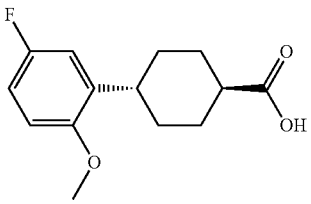 [SMILES: COc1ccc(F)cc1[C@H]1CC[C@H](C(=O)O)CC1]

The title compound was obtained as white solid in 40% yield from 4-(5-fluoro-2-methoxy-phenyl)-cyclohexanecarboxylic acid ethyl ester according to general procedure (IV). MS m/e: 251 ([M−H]⁻)

4-Aryl-cyclohexanecarboxylic acid 8 cis/trans-4-(3-Cyano-phenyl)-cyclohexanecarboxylic acid (3:1)

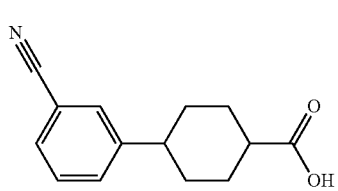 [SMILES: N#Cc1cccc(C2CCC(C(=O)O)CC2)c1]

A solution of cis/trans-4-(3-cyano-phenyl)-cyclohexanecarboxylic acid ethyl ester (3:1) (0.50 g, 1.9 mmol) in 1,4-dioxane (19 ml) and 2 M aqueous sodium hydroxide solution (9.5 ml, 19 mmol) was stirred for 20 h at room temperature. The reaction mixture was diluted with tert-butyl methyl ether and extracted with two portions of 1M aqueous sodium hydroxide solution. The combined aqueous layers were acidified to pH 1-2 with concentrated hydrochloric acid and extracted with three portions of tert-butyl methyl ether. The combined organic extracts were dried over anhydrous sodium sulfate and concentrated in vacuo to give the title compound as off-white solid in quantitative yield. MS m/e: 228 ([M−H]⁻)

Hydrazide Intermediates of Formula II

General Procedure (VI)

To a solution of a 4-aryl-cyclohexanecarboxylic acid intermediate of formula VII (1 eq) and triethylamine (1.05 eq) in tetrahydrofuran (0.2 M) is added ethyl chloroformate (1.05 eq) at 0° C. The reaction mixture is stirred at 0° C. for 1 h. The ammonium salts are removed by filtration. The filtrate is added to a cold solution of hydrazine hydrate (2 eq) in methanol (0.2 M). The reaction mixture is stirred at room temperature for 2-16 h. The solvent is evaporated under reduced pressure, and the residue is partitioned between an organic solvent such as ethyl acetate or dichloromethane and water. The organic layer is separated. The aqueous layer is extracted with two or three portions of organic solvent. The combined organic layers are dried over anhydrous sodium sulfate and concentrated in vacuo to give a hydrazide intermediate of formula II, which is used in the next step without further purification.

Hydrazide 1 trans-4-Phenyl-cyclohexanecarboxylic acid hydrazide

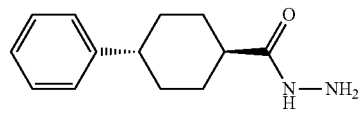 [SMILES: NNC(=O)[C@H]1CC[C@H](c2ccccc2)CC1]

The title compound was obtained as white solid in 89% yield from trans-4-phenyl-cyclohexanecarboxylic acid according to general procedure (VI). MS m/e: 219 (M+H⁺)

Hydrazide 2 cis-4-(4-Fluoro-phenyl)-cyclohexanecarboxylic acid hydrazide

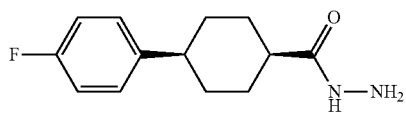 [SMILES: NNC(=O)[C@H]1CC[C@@H](c2ccc(F)cc2)CC1]

The title compound was obtained as amorphous white solid in 91% yield from cis-4-(4-fluoro-phenyl)-cyclohexanecarboxylic acid according to general procedure (VI). MS m/e: 237 (M+H⁺)

Hydrazide 3 trans-4-(4-Fluoro-phenyl)-cyclohexanecarboxylic acid hydrazide

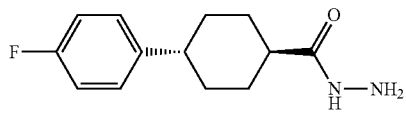 [SMILES: NNC(=O)[C@H]1CC[C@H](c2ccc(F)cc2)CC1]

The title compound was obtained as off-white solid in 94% yield from trans-4-(4-fluoro-phenyl)-cyclohexanecarboxylic acid according to general procedure (VI). MS m/e: 237 (M+H⁺)

Hydrazide 4 trans-4-(3-Trifluoromethoxy-phenyl)-cyclohexanecarboxylic acid hydrazide

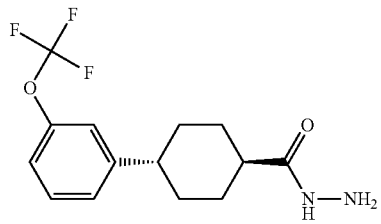 [SMILES: NNC(=O)[C@H]1CC[C@H](c2cccc(OC(F)(F)F)c2)CC1]

The title compound was obtained as light yellow solid in 91% yield from trans-4-(3-trifluoromethoxy-phenyl)-cyclo hexanecarboxylic acid according to general procedure (VI). MS m/e: 303 (M+H⁺)

Hydrazide 5 trans-4-(2-Chloro-3-fluoro-phenyl)-cyclohexanecarboxylic acid hydrazide

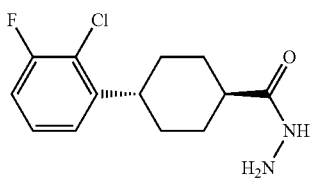 [SMILES: NNC(=O)[C@H]1CC[C@H](c2cccc(F)c2Cl)CC1]

The title compound was obtained as white solid in 95% yield from trans-4-(2-chloro-3-fluoro-phenyl)-cyclohexanecarboxylic acid according to general procedure (VI). MS m/e: 271 (M+H⁺)

Hydrazide 6 trans-4-Naphthalen-1-yl-cyclohexanecarboxylic acid hydrazide

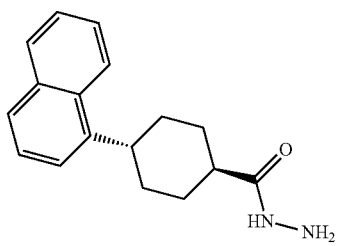 [SMILES: NNC(=O)[C@H]1CC[C@H](c2cccc3ccccc32)CC1]

The title compound was obtained as white solid in 93% yield from trans-4-naphthalen-1-yl-cyclohexanecarboxylic acid according to general procedure (VI). MS m/e: 269 (M+H⁺)

Hydrazide 7 trans-4-(5-Fluoro-2-methoxy-phenyl)-cyclohexanecarboxylic acid hydrazide

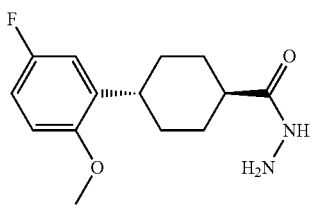 [SMILES: COc1ccc(F)cc1[C@H]1CC[C@H](C(=O)NN)CC1]

The title compound was obtained as white solid in 95% yield from trans-4-(5-fluoro-2-methoxy-phenyl)-cyclohexanecarboxylic acid according to general procedure (VI). MS m/e: 267 (M+H⁺)

Hydrazide 8 cis/trans-4-(3-Cyano-phenyl)-cyclohexanecarboxylic acid hydrazide (3:1)

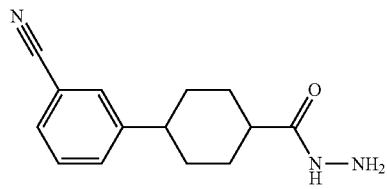 [SMILES: N#Cc1cccc(C2CCC(C(=O)NN)CC2)c1]

The title compound was obtained as off-white solid in 95% yield from cis/trans-4-(3-cyano-phenyl)-cyclohexanecarboxylic acid according to general procedure (VI). MS m/e: 244 (M+H⁺)

Hydrazide 9 cis/trans-4-Hydroxy-cyclohexanecarboxylic acid hydrazide (2:1)

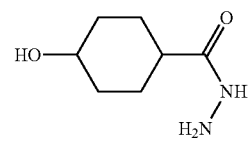

A mixture of cis/trans ethyl 4-hydroxycyclohexane carboxylate (5.0 g, 29 mmol) and hydrazine hydrate (1.4 g, 29 mmol) was heated at reflux for 24 h. Residual water was removed by azeotropic distillation with toluene. The residue was triturated from tert-butyl methyl ether. The precipitate was collected by filtration and dried in vacuo to give the title compound as white solid in 91% yield.

Thiolactam Intermediates of Formula III

7-Chloro-2-thioxo-1,2,3,5-tetrahydro-benzo[e][1,4] diazepine-4-carboxylic acid tert-butyl ester a) 4-Chloro-2-chloromethyl-1-nitro-benzene To a solution of 5-chloro-2-nitrobenzyl alcohol (80 g, 0.42 mol) and triethylamine (64 ml, 0.46 mol) in dichloromethane (840 ml) was added drop wise thionyl chloride (34 ml, 0.46 mol) during a period of 30 minutes while the internal temperature was kept below 32° C. by cooling with a water bath. The reaction mixture was stirred for 3 h. The solvent was evaporated and the residue was triturated in warm tert-butyl methyl ether (970 ml). The ammonium salts were removed by filtration and the filtrate was concentrated in vacuo to give the title compound (85 g, 99%) as brown oil which was used in the next step without purification. MS m/e: 205 (M⁺).

b) (5-Chloro-2-nitro-benzylamino)-acetic acid ethyl ester

A mixture of 4-chloro-2-chloromethyl-1-nitro-benzene (85 g, 0.41 mol), glycine ethyl ester hydrochloride (70 g, 0.50 mol) and triethylamine (121.4 ml, 0.8665 mol) in ethanol (1000 ml) was heated at reflux for 8 h. The solvent was evaporated and the residue was triturated in warm tert-butyl methyl ether. The ammonium salts were removed by filtration and the filtrate was concentrated in vacuo to give the title compound (111 g, 99%) as an amorphous brown solid which was used in the next step without purification. MS m/e: 273 (M+H$^+$).

c) [tert-Butoxycarbonyl-(5-chloro-2-nitro-benzyl)-amino]-acetic acid ethyl ester A solution of (5-chloro-2-nitro-benzylamino)-acetic acid ethyl ester (110 g, 0.403 mol), di-tert-butyl dicarbonate (180 g, 0.807 mol) and 4-N,N-dimethylaminopyridine (2.51 g, 0.0202 mol) in dichloromethane (1200 ml) was stirred for 2 h at 0° C. and further 16 h at room temperature. The solvent was evaporated and the crude product was purified by flash chromatography with a cyclohexane/ethyl acetate mixture as eluent to give the title compound (76.4 g, 51%) as light yellow viscous oil. MS m/e: 373 (M+H$^+$).

d) [(2-Amino-5-chloro-benzyl)-tert-butoxycarbonyl-amino]-acetic acid ethyl ester To a solution of [tert-butoxycarbonyl-(5-chloro-2-nitro-benzyl)-amino]-acetic acid ethyl ester (69.0 g, 0.186 mol) in ethyl acetate (1200 ml) was added zinc bromide (8.5 g, 0.037 mol). The reaction mixture was purged with argon after 15 minutes. After addition of the palladium catalyst (10% on activated charcoal, 7.9 g, 0.0074 mol) the mixture was hydrogenated at ambient pressure during a period of ca. 48 h until ca. 13 l of hydrogen gas had been consumed. The catalyst was removed by filtration and the filtrate was washed with two portions of saturated aqueous sodium bicarbonate solution and brine, each. The organic layer was dried over anhydrous sodium sulfate and concentrated in vacuo to give the title compound (60.6 g, 95.5%) as yellow waxy solid. MS m/e: 343 (M+H$^+$).

e) 7-Chloro-2-oxo-1,2,3,5-tetrahydro-benzo[1,4]diazepine-4-carboxylic acid tert-butyl ester To a solution of [(2-amino-5-chloro-benzyl)-tert-butoxycarbonyl-amino]-acetic acid ethyl ester (60 g, 0.18 mol) in tetrahydrofuran (600 ml) was added potassium tert-butoxide (22 g, 0.19 mol) in small portions at 5° C. under cooling on an ice-water batch. After completed addition the cooling bath was removed and reaction mixture was stirred for 3 h at room temperature followed by addition of water (400 ml), saturated aqueous ammonium chloride solution (280 ml) and ethyl acetate (800 ml). After 10 minutes the precipitate was collected by filtration. The layers were separated from the filtrate, dried over anhydrous sodium sulfate and concentrated in vacuo. The residue was combined with the precipitate, which had previously been collected by filtration, and crystallized from hot ethyl acetate to give the title compound (46 g, 88%) as white solid. MS m/e: 295 (M−H$^+$).

f) 7-Chloro-2-thioxo-1,2,3,5-tetrahydro-benzo[e][1,4]diazepine-4-carboxylic acid tert-butyl ester A mixture of 7-chloro-2-oxo-1,2,3,5-tetrahydro-benzo[1,4]diazepine-4-carboxylic acid tert-butyl ester (41.1 g, 0.139 mol) and 2,4-bis-(4-methoxyphenyl)-1,3,2,4-dithiadiphosphetane-2,4-disulfide (31.5 g, 0.0763 mol) in tetrahydrofuran (1100 ml) was heated at reflux for 3 h. The solvent was evaporated and the residue was triturated in tert-butyl methyl ether. The precipitate was removed by filtration and the filtrate was concentrated to dryness. The residue was crystallized from hot ethanol to give the title compound (37.5 g, 86.4%) as light yellow solid. MS m/e: 311 (M−H$^+$).

7-Fluoro-2-thioxo-1,2,3,5-tetrahydro-benzo[e][1,4]diazepine-4-carboxylic acid tert-butyl ester The title compound was obtained as light yellow solid in comparable yields according to the procedures described above for the synthesis of 7-chloro-2-thioxo-1,2,3,5-tetrahydro-benzo[e][1,4]diazepine-4-carboxylic acid tert-butyl ester using 5-fluoro-2-nitrobenzyl alcohol instead of 5-chloro-2-nitrobenzyl alcohol in step a). MS m/e: 297 (M−H$^+$).

General Procedure (VII): Condensation of Hydrazide and Thiolactam to Triazole A mixture of a hydrazide of formula II (1-1.5 eq) and a thiolactam of formula III (1 eq) in n-butanol (0.1-0.2 M) is heated at reflux for 16-72 h. After cooling to room temperature the solvent is evaporated and the residue is purified by flash-chromatography to give a compound of formula I. When a thiolactam of formula III-1 (compounds of formula III in which R$^1$ is tert-butoxycarbonyl) is used the N-tert-butoxycarbonyl group of the resulting triazole product of formula I-1 can be partially or completely cleaved thermally, and a secondary amine of formula I-2 is obtained in addition or as the sole product.

General Procedure (VIII): Cleavage of N-tert-butoxycarbonyl (N-BOC) Group

A solution of an N-BOC derivative of formula I-1 (1 eq) in 1.25 M methanolic or 1.5 M ethanolic hydrogen chloride solution (10-20 eq HCl) is heated at 50° C. for 15-60 minutes. After cooling to room temperature the reaction mixture is concentrated in vacuo to give a secondary amine of formula I-2 as hydrochloride salt. Optionally the free base can be obtained by partitioning the hydrochloride salt between 1 M aqueous sodium hydroxide solution and an organic solvent, e.g. ethyl acetate or dichloromethane. The layers are separated and the aqueous layer is extracted with two portions of the organic solvent. The combined organic layers are dried over anhydrous sodium sulfate, filtered and concentrated in vacuo to give the free base of a compound of formula I-2.

General Procedure (IX): Reductive N-Alkylation

A mixture of a compound of formula I-2 as free base or as hydrochloride salt (1 eq, 0.1-0.2 M), triethylamine (1 eq when the hydrochloride salt of a compound of formula I-2 is used) and an aldehyde or ketone (8 eq) in methanol is heated at reflux for 2-6 h. After cooling to 0° C. sodium cyanoborohydride (2-3 eq) is added. The reaction mixture is stirred for 3-16 h at room temperature and quenched with 1 M aqueous sodium hydroxide solution. The aqueous layer is extracted with ethyl acetate. The combined organic layers are dried over anhydrous sodium sulfate and concentrated in vacuo. Flash chromatography gives an N-alkyl of formula I.

Example 1 trans-8-Chloro-1-(4-phenyl-cyclohexyl)-4H,6H-2,3,5,10b-tetraaza-benzo[e]azulene-5-carboxylic acid tert-butyl ester The title compound was obtained as white solid in 74% yield using general procedure (VII). Hydrazide: trans-4-Phenyl-cyclohexanecarboxylic acid hydrazide Thiolactam: 7-Chloro-2-thioxo-1,2,3,5-tetrahydro-benzo[e][1,4]diazepine-4-carboxylic acid tert-butyl ester. MS m/e: 479 (M+H⁺)

Example 2 trans-8-Chloro-1-(4-phenyl-cyclohexyl)-5,6-dihydro-4H-2,3,5,10b-tetraaza-benzo[e]azulene hydrochloride The title compound was obtained as white solid in quantitative yield from trans-8-chloro-1-(4-phenyl-cyclohexyl)-4H,6H-2,3,5,10b-tetraaza-benzo[e]azulene-5-carboxylic acid tert-butyl ester using general procedure (VIII). MS m/e: 379 (M+H⁺)

Example 3 trans-8-Chloro-5-methyl-1-(4-phenyl-cyclohexyl)-5,6-dihydro-4H-2,3,5,10b-tetraaza-benzo[e]azulene The title compound was obtained as off-white solid in 88% yield from trans-8-chloro-1-(4-phenyl-cyclohexyl)-5,6-dihydro-4H-2,3,5,10b-tetraaza-benzo[e]azulene hydrochloride and paraformaldehyde using general procedure (IX). MS m/e: 393 (M+H⁺)

Example 4 cis-8-Chloro-5-methyl-1-(4-o-tolyl-cyclohexyl)-5,6-dihydro-4H-2,3,5,10b-tetraaza-benzo[e]azulene and

Example 5 trans-8-Chloro-5-methyl-1-(4-o-tolyl-cyclohexyl)-5,6-dihydro-4H-2,3,5,10b-tetraaza-benzo[e]azulene and

Example 6 cis-5-Methyl-1-(4-o-tolyl-cyclohexyl)-5,6-dihydro-4H-2,3,5,10b-tetraaza-benzo[e]azulene a) cis/trans-8-Chloro-1-(4-hydroxy-cyclohexyl)-4H,6H-2,3,5,10b-tetraaza-benzo[e]azulene-5-carboxylic acid tert-butyl ester

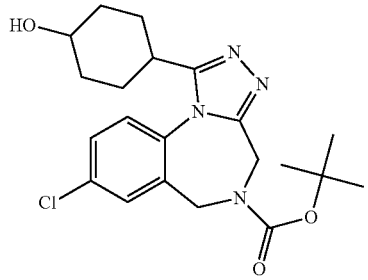 [SMILES: CC(C)(C)OC(=O)N1Cc2cc(Cl)ccc2-n2c(nnc2C2CCC(O)CC2)C1]

The title compound was obtained as white foam in 64% yield using general procedure (VII). Hydrazide: cis/trans-4-Hydroxy-cyclohexanecarboxylic acid hydrazide Thiolactam: 7-Chloro-2-thioxo-1,2,3,5-tetrahydro-benzo[e][1,4]diazepine-4-carboxylic acid tert-butyl ester MS m/e: 419 (M+H⁺)

b) 8-Chloro-1-(4-oxo-cyclohexyl)-4H,6H-2,3,5,10b-tetraaza-benzo[e]azulene-5-carboxylic acid tert-butyl ester

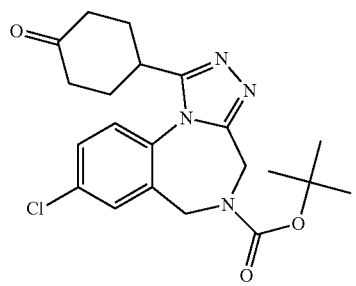 [SMILES: CC(C)(C)OC(=O)N1Cc2cc(Cl)ccc2-n2c(nnc2C2CCC(=O)CC2)C1]

To a solution of oxalyl chloride (0.11 ml, 1.3 mmol) in dichloromethane (8 ml) was added dimethylsulfoxide (0.21 ml, 2.6 mmol) at −60° C. The mixture was stirred for 5 minutes at −50° C. A solution of cis/trans-8-chloro-1-(4-hydroxy-cyclohexyl)-4H,6H-2,3,5,10b-tetraaza-benzo[e]azulene-5-carboxylic acid tert-butyl ester (0.046 g, 1.1 mmol) in dichloromethane (3 ml) was added at −65° C. Stirring for 30 minutes was followed by addition of triethylamine (0.77 ml, 5.5 mmol). The cooling bath was removed after 5 minutes, and the reaction mixture was stirred for 1 h. The reaction mixture was washed with one portion of aqueous saturated ammonium chloride solution. The aqueous layer was extracted with three portions of tert-butyl methyl ether. The combined organic layers were dried over anhydrous sodium sulfate and concentrated in vacuo. Flash-chromatography with n-heptane/ethyl acetate as eluent gave the title compound (0.41 g, 90%) as white solid. MS m/e: 417 (M+H⁺)

c) 8-Chloro-1-(4-hydroxy-4-o-tolyl-cyclohexyl)-4H,6H-2,3,5,10b-tetraaza-benzo[e]azulene-5-carboxylic acid tert-butyl ester

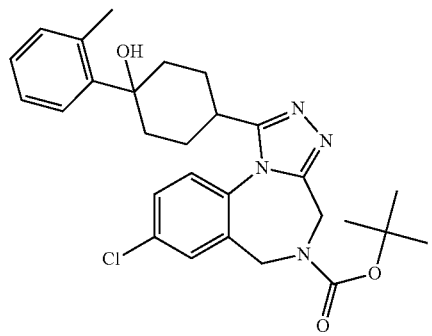 [SMILES: Cc1ccccc1C1(O)CCC(c2nnc3n2-c2ccc(Cl)cc2CN(C(=O)OC(C)(C)C)C3)CC1]

To a solution of 8-chloro-1-(4-oxo-cyclohexyl)-4H,6H-2,3,5,10b-tetraaza-benzo[e]azulene-5-carboxylic acid tert-butyl ester (0.2 g, 0.5 mmol) in dry tetrahydrofuran (5 ml) was added a 1M o-tolylmagnesium chloride solution in tetrahydrofuran (0.5 ml, 0.5 mmol) at room temperature. The reaction mixture was stirred for 2 h. The reaction mixture was quenched with aqueous saturated ammonium chloride solution and extracted with two portions of ethyl acetate. The combined organic layers were washed with one portion of brine, dried over anhydrous sodium sulfate and concentrated in vacuo. Flash-chromatography with n-heptane/ethyl acetate as eluent gave the title compound (0.17 g, 70%) as white solid. MS m/e: 509 (M+H$^+$)

d) (RS)-8-Chloro-1-(4-o-tolyl-cyclohex-3-enyl)-5,6-dihydro-4H-2,3,5,10b-tetraaza-benzo[e]azulene hydrochloride

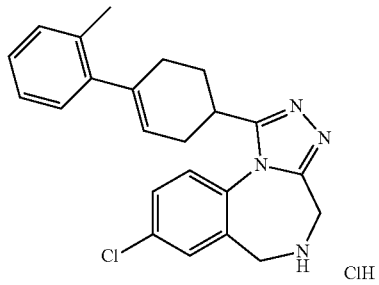 [SMILES: Cc1ccccc1C1=CCC(c2nnc3n2-c2ccc(Cl)cc2CNC3)CC1 ; Cl]

The title compound was obtained as white solid in quantitative yield from cis/trans-8-chloro-1-(4-hydroxy-4-o-tolyl-cyclohexyl)-4H,6H-2,3,5,10b-tetraaza-benzo[e]azulene-5-carboxylic acid tert-butyl ester using general procedure (VIII). MS m/e: 391 (M+H$^+$)

e) (RS)-8-Chloro-5-methyl-1-(4-o-tolyl-cyclohex-3-enyl)-5,6-dihydro-4H-2,3,5,10b-tetraaza-benzo[e]azulene

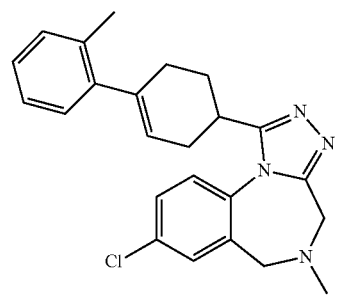 [SMILES: Cc1ccccc1C1=CCC(c2nnc3n2-c2ccc(Cl)cc2CN(C)C3)CC1]

The title compound was obtained as white solid in 79% yield from (RS)-8-chloro-1-(4-o-tolyl-cyclohex-3-enyl)-5,6-dihydro-4H-2,3,5,10b-tetraaza-benzo[e]azulene hydrochloride and paraformaldehyde using general procedure (IX). MS m/e: 405 (M+H$^+$)

f) cis-8-Chloro-5-methyl-1-(4-o-tolyl-cyclohexyl)-5,6-dihydro-4H-2,3,5,10b-tetraaza-benzo[e]azulene and g) trans-8-Chloro-5-methyl-1-(4-o-tolyl-cyclohexyl)-5,6-dihydro-4H-2,3,5,10b-tetraaza-benzo[e]azulene and h) cis-5-Methyl-1-(4-o-tolyl-cyclohexyl)-5,6-dihydro-4H-2,3,5,10b-tetraaza-benzo[e]azulene A solution of (RS)-8-chloro-5-methyl-1-(4-o-tolyl-cyclohex-3-enyl)-5,6-dihydro-4H-2,3,5,10b-tetraaza-benzo[e]azulene (0.10 g, 0.25 mmol) in acetic acid (2.5 ml) was purged with argon. After addition of platinum(IV) oxide (0.017 g, 0.075 mmol) the reaction vessel was filled with hydrogen. The reaction mixture was stirred under an atmosphere of hydrogen (1 bar) at room temperature for 48 h. The catalyst was removed by filtration over Decalite®. The filtrate was partitioned between ethyl acetate and aqueous 2 M sodium carbonate solution. The organic layer was collected. The aqueous layer was extracted with one portion of ethyl acetate. The combined organic layers were dried over anhydrous sodium sulfate and concentrated to dryness. Consecutive purification by flash column chromatography over aminopropyl modified silica gel with n-heptane/ethyl acetate as eluent and HPLC using a Chiralpac® AD column with n-heptane/2-propanol as eluent gave cis-8-chloro-5-methyl-1-(4-o-tolyl-cyclohexyl)-5,6-dihydro-4H-2,3,5,10b-tetraaza-benzo[e]azulene as white solid in 20% yield, trans-8-chloro-5-methyl-1-(4-o-tolyl-cyclohexyl)-5,6-dihydro-4H-2,3,5,10b-tetraaza-benzo[e]azulene as white solid in 11% yield and cis-5-methyl-1-(4-o-tolyl-cyclohexyl)-5,6-dihydro-4H-2,3,5,10b-tetraaza-benzo[e]azulene as off-white solid in 8% yield.

cis-8-Chloro-5-methyl-1-(4-o-tolyl-cyclohexyl)-5,6-dihydro-4H-2,3,5,10b-tetraaza-benzo[e]azulene, MS m/e: 407 (M+H$^+$)

trans-8-Chloro-5-methyl-1-(4-o-tolyl-cyclohexyl)-5,6-dihydro-4H-2,3,5,10b-tetraaza-benzo[e]azulene, MS m/e: 407 (M+H$^+$)

cis-5-Methyl-1-(4-o-tolyl-cyclohexyl)-5,6-dihydro-4H-2,3,5,10b-tetraaza-benzo[e]azulene MS m/e: 373 (M+H$^+$)

Example 7 cis-8-Chloro-1-[4-(4-fluoro-phenyl)-cyclohexyl]-4H,6H-2,3,5,10b-tetraaza-benzo[e]azulene- The title compound was obtained as light yellow solid in 68% yield using general procedure (VII). Hydrazide: cis-4-(4-Fluoro-phenyl)-cyclohexanecarboxylic acid hydrazide Thiolactam: 7-Chloro-2-thioxo-1,2,3,5-tetrahydro-benzo[e][1,4]diazepine-4-carboxylic acid tert-butyl ester. MS m/e: 497 (M+H$^+$)

Example 8 cis-8-Chloro-1-[4-(4-fluoro-phenyl)-cyclohexyl]-5,6-dihydro-4H-2,3,5,10b-tetraaza-benzo[e]azulene hydrochloride The title compound was obtained as off-white solid in quantitative yield from cis-8-chloro-1-[4-(4-fluoro-phenyl)-cyclohexyl]-4H,6H-2,3,5,10b-tetraaza-benzo[e]azulene-5-carboxylic acid tert-butyl ester using general procedure (VIII). MS m/e: 397 (M+H$^+$)

Example 9 cis-8-Chloro-1-[4-(4-fluoro-phenyl)-cyclohexyl]-5-methyl-5,6-dihydro-4H-2,3,5,10b-tetraaza-benzo[e]azulene The title compound was obtained as white solid in 77% yield from cis-8-chloro-1-[4-(4-fluoro-phenyl)-cyclohexyl]-

5,6-dihydro-4H-2,3,5,10b-tetraaza-benzo[e]azulene hydrochloride and paraformaldehyde using general procedure (IX). MS m/e: 411 (M+H$^+$).

Example 10 trans-8-Chloro-1-[4-(4-fluoro-phenyl)-cyclohexyl]-4H,6H-2,3,5,10b-tetraaza-benzo[e]azulene-5-carboxylic acid tert-butyl ester The title compound was obtained as white solid in 31% yield using general procedure (VII). Hydrazide: trans-4-(4-Fluoro-phenyl)-cyclohexanecarboxylic acid hydrazide Thiolactam: 7-Chloro-2-thioxo-1,2,3,5-tetrahydro-benzo[e][1,4]diazepine-4-carboxylic acid tert-butyl ester. MS m/e: 497 (M+H$^+$)

Example 11 trans-8-Chloro-1-[4-(4-fluoro-phenyl)-cyclohexyl]-5,6-dihydro-4H-2,3,5,10b-tetraaza-benzo[e]azulene hydrochloride The title compound was obtained as off-white solid in quantitative yield from trans-8-chloro-1-[4-(4-fluoro-phenyl)-cyclohexyl]-4H,6H-2,3,5,10b-tetraaza-benzo[e]azulene-5-carboxylic acid tert-butyl ester using general procedure (VIII). MS m/e: 397 (M+H$^+$)

Example 12 trans-8-Chloro-1-[4-(4-fluoro-phenyl)-cyclohexyl]-5-methyl-5,6-dihydro-4H-2,3,5,10b-tetraaza-benzo[e]azulene The title compound was obtained as white solid in 41% yield from trans-8-chloro-1-[4-(4-fluoro-phenyl)-cyclohexyl]-5,6-dihydro-4H-2,3,5,10b-tetraaza-benzo[e]azulene hydrochloride and paraformaldehyde using general procedure (IX). MS m/e: 411 (M+H$^+$)

Example 13 trans-8-Chloro-1-[4-(3-trifluoromethoxy-phenyl)-cyclohexyl]-4H,6H-2,3,5,10b-tetraaza-benzo[e]azulene-5-carboxylic acid tert-butyl ester The title compound was obtained as white solid in 44% yield using general procedure (VII). Hydrazide: trans-4-(3-Trifluoromethoxy-phenyl)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 563 (M+H$^+$)

Example 14 trans-8-Chloro-1-[4-(3-trifluoromethoxy-phenyl)-cyclohexyl]-5,6-dihydro-4H-2,3,5,10b-tetraaza-benzo[e]azulene hydrochloride The title compound was obtained as white solid in quantitative yield from trans-8-chloro-1-[4-(3-trifluoromethoxy-phenyl)-cyclohexyl]-4H,6H-2,3,5,10b-tetraaza-benzo[e]azulene-5-carboxylic acid tert-butyl ester using general procedure (VIII). MS m/e: 463 (M+H$^+$)

Example 15 trans-8-Chloro-5-methyl-1-[4-(3-trifluoromethoxy-phenyl)-cyclohexyl]-5,6-dihydro-4H-2,3,5,10b-tetraaza-benzo[e]azulene The title compound was obtained as white solid in 72% yield from trans-8-chloro-1-[4-(3-trifluoromethoxy-phenyl)-cyclohexyl]-5,6-dihydro-4H-2,3,5,10b-tetraaza-benzo[e]azulene hydrochloride and paraformaldehyde using general procedure (IX). MS m/e: 477 M+H$^+$)

Example 16 trans-8-Chloro-1-[4-(2-chloro-3-fluoro-phenyl)-cyclohexyl]-4H,6H-2,3,5,10b-tetraaza-benzo[e]azulene-5-carboxylic acid tert-butyl ester The title compound was obtained as white solid in 68% yield using general procedure (VII). Hydrazide: trans-4-(2-Chloro-3-fluoro-phenyl)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 531 (M+H$^+$)

Example 17 trans-8-Chloro-1-[4-(2-chloro-3-fluoro-phenyl)-cyclohexyl]-5,6-dihydro-4H-2,3,5,10b-tetraaza-benzo[e]azulene hydrochloride The title compound was obtained as white solid in quantitative yield from trans-8-chloro-1-[4-(2-chloro-3-fluoro-phenyl)-cyclohexyl]-4H,6H-2,3,5,10b-tetraaza-benzo[e]azulene-5-carboxylic acid tert-butyl ester using general procedure (VIII). MS m/e: 431 (M+H$^+$)

Example 18 trans-8-Chloro-1-[4-(2-chloro-3-fluoro-phenyl)-cyclohexyl]-5-methyl-5,6-dihydro-4H-2,3,5,10b-tetraaza-benzo[e]azulene The title compound was obtained as white solid in 54% yield from trans-8-chloro-1-[4-(2-chloro-3-fluoro-phenyl)-cyclohexyl]-5,6-dihydro-4H-2,3,5,10b-tetraaza-benzo[e]azulene hydrochloride and paraformaldehyde using general procedure (IX). MS m/e: 445 (M+H$^+$)

Example 19 trans-8-Chloro-1-(4-naphthalen-1-yl-cyclohexyl)-4H,6H-2,3,5,10b-tetraaza-benzo[e]azulene-5-carboxylic acid tert-butyl ester The title compound was obtained as white solid in 64% yield using general procedure (VII). Hydrazide: trans-4-Naphthalen-1-yl-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 529 (M+H$^+$)

Example 20 trans-8-Chloro-1-(4-naphthalen-1-yl-cyclohexyl)-5,6-dihydro-4H-2,3,5,10b-tetraaza-benzo[e]azulene hydrochloride The title compound was obtained as white solid in quantitative yield from trans-8-chloro-1-(4-naphthalen-1-yl-cyclohexyl)-4H,6H-2,3,5,10b-tetraaza-benzo[e]azulene-5-carboxylic acid tert-butyl ester using general procedure (VIII). MS m/e: 429 (M+H$^+$)

Example 21 trans-8-Chloro-5-methyl-1-(4-naphthalen-1-yl-cyclohexyl)-5,6-dihydro-4H-2,3,5,10b-tetraaza-benzo[e]azulene The title compound was obtained as white solid in 62% yield from trans-8-chloro-1-(4-naphthalen-1-yl-cyclohexyl)-5,6-dihydro-4H-2,3,5,10b-tetraaza-benzo[e]azulene hydrochloride and paraformaldehyde using general procedure (IX). MS m/e: 443 M+H$^+$)

Example 22 trans-8-Chloro-1-[4-(5-fluoro-2-methoxy-phenyl)-cyclohexyl]-4H,6H-2,3,5,10b-tetraaza-benzo[e]azulene-5-carboxylic acid tert-butyl ester The title compound was obtained as white solid in 87% yield using general procedure (VII). Hydrazide: trans-4-(5-Fluoro-2-methoxy-phenyl)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 527 (M+H$^+$)

Example 23 trans-8-Chloro-1-[4-(5-fluoro-2-methoxy-phenyl)-cyclohexyl]-5,6-dihydro-4H-2,3,5,10b-tetraaza-benzo[e]azulene hydrochloride The title compound was obtained as white solid in quantitative yield from trans-8-chloro-1-[4-(5-fluoro-2-methoxy-phenyl)-cyclohexyl]-4H,6H-2,3,5,10b-tetraaza-benzo[e]azulene-5-carboxylic acid tert-butyl ester using general procedure (VIII). MS m/e: 427 M+H$^+$)

Example 24 trans-8-Chloro-1-[4-(5-fluoro-2-methoxy-phenyl)-cyclohexyl]-5-methyl-5,6-dihydro-4H-2,3,5,10b-tetraaza-benzo[e]azulene The title compound was obtained as white solid in 78% yield from trans-8-chloro-1-[4-(5-fluoro-2-methoxy-phenyl)-cyclohexyl]-5,6-dihydro-4H-2,3,5,10b-tetraaza-benzo[e]azulene hydrochloride and paraformaldehyde using general procedure (IX). MS m/e: 441 (M+H$^+$)

Example 25 trans-8-Chloro-1-[4-(3-cyano-phenyl)-cyclohexyl]-4H,6H-2,3,5,10b-tetraaza-benzo[e]azulene-5-carboxylic acid tert-butyl ester The title compound was obtained as white solid in 28% yield using general procedure (VII). Hydrazide: cis/trans-4-(3-Cyano-phenyl)-cyclohexanecarboxylic acid hydrazide (3:1)
Thiolactam: 7-Chloro-2-thioxo-1,2,3,5-tetrahydro-benzo[e][1,4]diazepine-4-carboxylic acid tert-butyl ester. MS m/e: 504 (M+H$^+$)

Example 26 trans-3-[4-(8-Chloro-5,6-dihydro-4H-2,3,5,10b-tetraaza-benzo[e]azulen-1-yl)-cyclohexyl]-benzonitrile hydrochloride The title compound was obtained as white solid in quantitative yield from trans-8-chloro-1-[4-(3-cyano-phenyl)-cyclohexyl]-4H,6H-2,3,5,10b-tetraaza-benzo[e]azulene-5-carboxylic acid tert-butyl ester using general procedure (VIII). MS m/e: 404 (M+H$^+$)

Example 27 trans-3-[4-(8-Chloro-5-methyl-5,6-dihydro-4H-2,3,5,10b-tetraaza-benzo[e]azulen-1-yl)-cyclohexyl]-benzonitrile The title compound was obtained as white solid in 66% yield from trans-3-[4-(8-chloro-5,6-dihydro-4H-2,3,5,10b-tetraaza-benzo[e]azulen-1-yl)-cyclohexyl]-benzonitrile hydrochloride and paraformaldehyde using general procedure (IX). MS m/e: 418 (M+H$^+$)

Example 28 trans-1-[8-Chloro-1-(4-phenyl-cyclohexyl)-4H,6H-2,3,5,10b-tetraaza-benzo[e]azulen-5-yl]-ethanone To a solution of trans-8-chloro-1-(4-phenyl-cyclohexyl)-5,6-dihydro-4H-2,3,5,10b-tetraaza-benzo[e]azulene hydrochloride (0.090 g, 0.22 mmol) and triethylamine (0.063 ml, 0.46 mmol) in dichloromethane (5 ml) was added acetyl chloride (0.017 ml, 0.24 mmol) at room temperature. After stirring for 19 h the reaction mixture was concentrated in vacuo. Flash-chromatography with n-heptane/ethyl acetate as eluent gave the title compound (0.082 g, 90%) as white solid. MS m/e: 421 (M+H$^+$)

Example 29 trans-8-Chloro-5-methanesulfonyl-1-(4-phenyl-cyclohexyl)-5,6-dihydro-4H-2,3,5,10b-tetraaza-benzo[e]azulene To a solution of trans-8-chloro-1-(4-phenyl-cyclohexyl)-5,6-dihydro-4H-2,3,5,10b-tetraaza-benzo[e]azulene hydrochloride (0.065 g, 0.16 mmol) and triethylamine (0.046 ml, 0.33 mmol) in dichloromethane (5 ml) was added methanesulphonyl chloride (0.013 ml, 0.17 mmol) at room temperature. After stirring for 19 h the reaction mixture was concentrated in vacuo. Flash-chromatography with n-heptane/ethyl acetate as eluent gave the title compound (0.043 g, 60%) as white solid. MS m/e: 457 (M+H$^+$).

Example 30 trans-8-Chloro-5-isopropyl-1-(4-phenyl-cyclohexyl)-5,6-dihydro-4H-2,3,5,10b-tetraaza-benzo[e]azulene The title compound was obtained as white solid in 80% yield from trans-8-chloro-1-(4-phenyl-cyclohexyl)-5,6-dihydro-4H-2,3,5,10b-tetraaza-benzo[e]azulene hydrochloride and acetone using general procedure (IX). MS m/e: 421 (M+H$^+$)

Example 31 trans-8-Chloro-1-(4-phenyl-cyclohexyl)-5-pyridin-2-ylmethyl-5,6-dihydro-4H-2,3,5,10b-tetraaza-benzo[e]azulene To a mixture of trans-8-chloro-1-(4-phenyl-cyclohexyl)-5,6-dihydro-4H-2,3,5,10b-tetraaza-benzo[e]azulene hydrochloride (0.065 g, 0.16 mmol) and potassium carbonate (0.073 ml, 0.53 mmol) in acetonitrile (1 ml) was added 2-(bromomethyl)pyridine hydrobromide (0.042 g, 0.16 mmol) at room temperature. Stirring for 65 h at 50° C. was followed by partitioning between 1 M aqueous sodium hydroxide solution (50 ml) and dichloromethane (50 ml). The layers were separated. The aqueous layer was extracted with one 50-ml portion of dichloromethane. The combined organic layers were dried over anhydrous sodium sulfate and concentrated in vacuo. Purification by flash-chromatography with n-heptane/ethyl acetate as eluent gave the title compound (0.058 g, 79%) as white solid. MS m/e: 471 (M+H$^+$)

Example 32 trans-2-[8-Chloro-1-(4-phenyl-cyclohexyl)-4H,6H-2,3,5,10b-tetraaza-benzo[e]azulen-5-yl]-ethanol The title compound was obtained as white solid in 13% yield from trans-8-chloro-1-(4-phenyl-cyclohexyl)-5,6-dihydro-4H-2,3,5,10b-tetraaza-benzo[e]azulene hydrochloride and glycol aldehyde using general procedure (IX). MS m/e: 423 (M+H$^+$)

Example 33 trans-8-Chloro-1-(4-phenyl-cyclohexyl)-5-pyridin-2-yl-5,6-dihydro-4H-2,3,5,10b-tetraaza-benzo[e]azulene A mixture of trans-8-chloro-1-(4-phenyl-cyclohexyl)-5,6-dihydro-4H-2,3,5,10b-tetraaza-benzo[e]azulene hydrochloride (0.10 g, 0.24 mmol), 2-bromopyridine (0.057 g, 0.36 mmol) and cetyltrimethylammonium bromide (0.0040 g, 0.012 mmol) in toluene (2 ml) and 50% aqueous sodium hydroxide solution (0.04 ml) was degassed by freeze/thaw cycles. Addition of bis(tri-t-butylphosphine)palladium (0.012 g, 0.024 mmol) was followed by stirring at 90° C. for 18 h. The reaction mixture was partitioned between water (50 ml) and dichloromethane (50 ml). The layers were separated. The aqueous layer was extracted with one 50-ml portion of dichloromethane. The combined organic layers were dried over anhydrous sodium sulfate and concentrated in vacuo. Purification by flash-chromatography with n-heptane/ethyl acetate and ethyl acetate/2-propanol as eluent gave the title compound (0.004 g, 4%) as colorless oil.

The invention claimed is:
1. A compound of the formula I

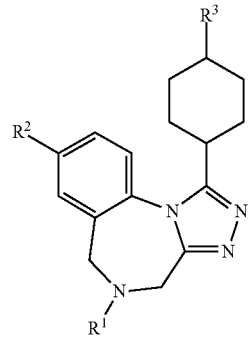

wherein
R$^1$ is selected from the group consisting of
i) H,
ii) —C$_{1-6}$-alkyl, unsubstituted or substituted by 1 to 5 substituents individually selected from the group consisting of OH, halogen, cyano and C$_{1-6}$-alkoxy,
iii) —(CH$_2$)$_p$—R$^4$, wherein
p is 0 or 1,
R$^4$ is phenyl or 5- or 6-membered heteroaryl, each of which is unsubstituted or substituted by 1 to 5 substituents individually selected from the group consisting of OH, halogen, cyano, C$_{1-6}$-alkoxy, halogen-C$_{1-6}$-alkyl, halogen-C$_{1-6}$-alkoxy and hydroxy-C$_{1-6}$-alkyl,
iv) —S(O)$_2$—C$_{1-6}$-alkyl, wherein the C$_{1-6}$-alkyl is unsubstituted or substituted by 1 to 5 substituents individually selected from the group consisting of OH, halogen, cyano and C$_{1-6}$-alkoxy,
v) —C(O)—C$_{1-6}$-alkyl, wherein the C$_{1-6}$-alkyl is unsubstituted or substituted by 1 to 5 substituents individually selected from the group consisting of OH, halogen, cyano and C$_{1-6}$-alkoxy, and
vi) —C(O)O—C$_{1-6}$-alkyl, wherein the C$_{1-6}$-alkyl is unsubstituted or substituted by 1 to 5 substituents individually selected from the group consisting of OH, halogen, cyano and C$_{1-6}$-alkoxy;
R$^2$ is selected from the group consisting of hydrogen and halogen; and
R$^3$ is aryl, unsubstituted or substituted by 1 to 5 substituents individually selected from the group consisting of OH, halogen, cyano, C$_{1-6}$-alkyl, C$_{1-6}$-alkoxy, halogen-C$_{1-6}$-alkyl, halogen-C$_{1-6}$-alkoxy and hydroxy-C$_{1-6}$-alkyl;
or a pharmaceutically acceptable salt thereof.
2. The compound of claim 1, wherein R$^1$ is selected from the group consisting of H, —C$_{1-6}$-alkyl, hydroxy-C$_{1-6}$-alkyl, —CH$_2$-6-membered heteroaryl, -6-membered heteroaryl, —S(O)$_2$—C$_{1-6}$-alkyl, —C(O)—C$_{1-6}$-alkyl and —C(O)O—C$_{1-6}$-alkyl.
3. The compound of claim 1, wherein R$^1$ is selected from the group consisting of H, —C$_{1-6}$-alkyl, hydroxy-C$_{1-6}$-alkyl, —CH$_2$-6-membered heteroaryl and —C(O)—C$_{1-6}$-alkyl.
4. The compound of claim 1, wherein R$^1$ is selected from the group consisting of H, methyl, acetonyl, isopropyl, pyridin-2-yl-methyl- and 2-hydroxy-ethyl.
5. The compound of claim 1, wherein R$^2$ is halogen.
6. The compound of claim 1, wherein R$^2$ is chloro.
7. The compound of claim 1, wherein R$^3$ is aryl, unsubstituted or substituted by 1 to 2 substituents individually selected from the group consisting of halogen, cyano, C$_{1-6}$-alkyl, C$_{1-6}$-alkoxy and halogen-C$_{1-6}$-alkoxy.
8. The compound of claim 1, wherein R$^3$ is aryl.

9. The compound of claim 8, wherein R³ is phenyl or naphth-1-yl.

10. The compound of claim 1, selected from the group consisting of
- (trans)-8-Chloro-1-(4-phenyl-cyclohexyl)-4H,6H-2,3,5,10b-tetraaza-benzo[e]azulene-5-carboxylic acid tert-butyl ester,
- (trans)-8-Chloro-1-(4-phenyl-cyclohexyl)-5,6-dihydro-4H-2,3,5,10b-tetraaza-benzo[e]azulene,
- (trans)-8-Chloro-5-methyl-1-(4-phenyl-cyclohexyl)-5,6-dihydro-4H-2,3,5,10b-tetraaza-benzo[e]azulene,
- (cis)-8-Chloro-5-methyl-1-(4-o-tolyl-cyclohexyl)-5,6-dihydro-4H-2,3,5,10b-tetraaza-benzo[e]azulene,
- (trans)-8-Chloro-5-methyl-1-(4-o-tolyl-cyclohexyl)-5,6-dihydro-4H-2,3,5,10b-tetraaza-benzo[e]azulene,
- (cis)-5-Methyl-1-(4-o-tolyl-cyclohexyl)-5,6-dihydro-4H-2,3,5,10b-tetraaza-benzo[e]azulene,
- (cis)-8-Chloro-1-[4-(4-fluoro-phenyl)-cyclohexyl]-4H,6H-2,3,5,10b-tetraaza-benzo[e]azulene-5-carboxylic acid tert-butyl ester,
- (cis)-8-Chloro-1-[4-(4-fluoro-phenyl)-cyclohexyl]-5,6-dihydro-4H-2,3,5,10b-tetraaza-benzo[e]azulene,
- (cis)-8-Chloro-1-[4-(4-fluoro-phenyl)-cyclohexyl]-5-methyl-5,6-dihydro-4H-2,3,5,10b-tetraaza-benzo[e]azulene,
- (trans)-8-Chloro-1-[4-(4-fluoro-phenyl)-cyclohexyl]-4H,6H-2,3,5,10b-tetraaza-benzo[e]azulene-5-carboxylic acid tert-butyl ester; and
- (trans)-8-Chloro-1-[4-(4-fluoro-phenyl)-cyclohexyl]-5,6-dihydro-4H-2,3,5,10b-tetraaza-benzo[e]azulene or a pharmaceutically acceptable salt thereof.

11. The compound of claim 1, selected from the group consisting of
- (trans)-8-Chloro-1-[4-(4-fluoro-phenyl)-cyclohexyl]-5-methyl-5,6-dihydro-4H-2,3,5,10b-tetraaza-benzo[e]azulene,
- (trans)-8-Chloro-1-[4-(3-trifluoromethoxy-phenyl)-cyclohexyl]-4H,6H-2,3,5,10b-tetraaza-benzo[e]azulene-5-carboxylic acid tert-butyl ester,
- (trans)-8-Chloro-1-[4-(3-trifluoromethoxy-phenyl)-cyclohexyl]-5,6-dihydro-4H-2,3,5,10b-tetraaza-benzo[e]azulene,
- (trans)-8-Chloro-5-methyl-1-[4-(3-trifluoromethoxy-phenyl)-cyclohexyl]-5,6-dihydro-4H-2,3,5,10b-tetraaza-benzo[e]azulene,
- (trans)-8-Chloro-1-[4-(2-chloro-3-fluoro-phenyl)-cyclohexyl]-4H,6H-2,3,5,10b-tetraaza-benzo[e]azulene-5-carboxylic acid tert-butyl ester,
- (trans)-8-Chloro-1-[4-(2-chloro-3-fluoro-phenyl)-cyclohexyl]-5,6-dihydro-4H-2,3,5,10b-tetraaza-benzo[e]azulene,
- (trans)-8-Chloro-1-[4-(2-chloro-3-fluoro-phenyl)-cyclohexyl]-5-methyl-5,6-dihydro-4H-2,3,5,10b-tetraaza-benzo[e]azulene,
- (trans)-8-Chloro-1-(4-naphthalen-1-yl-cyclohexyl)-4H,6H-2,3,5,10b-tetraaza-benzo[e]azulene-5-carboxylic acid tert-butyl ester,
- (trans)-8-Chloro-1-(4-naphthalen-1-yl-cyclohexyl)-5,6-dihydro-4H-2,3,5,10b-tetraaza-benzo[e]azulene,
- (trans)-8-Chloro-5-methyl-1-(4-naphthalen-1-yl-cyclohexyl)-5,6-dihydro-4H-2,3,5,10b-tetraaza-benzo[e]azulene, and
- (trans)-8-Chloro-1-[4-(5-fluoro-2-methoxy-phenyl)-cyclohexyl]-4H,6H-2,3,5,10b-tetraaza-benzo[e]azulene-5-carboxylic acid tert-butyl ester or a pharmaceutically acceptable salt thereof.

12. The compound of claim 1, selected from the group consisting of
- (trans)-8-Chloro-1-[4-(5-fluoro-2-methoxy-phenyl)-cyclohexyl]-5,6-dihydro-4H-2,3,5,10b-tetraaza-benzo[e]azulene,
- (trans)-8-Chloro-1-[4-(5-fluoro-2-methoxy-phenyl)-cyclohexyl]-5-methyl-5,6-dihydro-4H-2,3,5,10b-tetraaza-benzo[e]azulene,
- (trans)-8-Chloro-1-[4-(3-cyano-phenyl)-cyclohexyl]-4H,6H-2,3,5,10b-tetraaza-benzo[e]azulene-5-carboxylic acid tert-butyl ester,
- (trans)-3-[4-(8-Chloro-5,6-dihydro-4H-2,3,5,10b-tetraaza-benzo[e]azulen-1-yl)-cyclohexyl]-benzonitrile,
- (trans)-3-[4-(8-Chloro-5-methyl-5,6-dihydro-4H-2,3,5,10b-tetraaza-benzo[e]azulen-1-yl)-cyclohexyl]-benzonitrile,
- (trans)-1-[8-Chloro-1-(4-phenyl-cyclohexyl)-4H,6H-2,3,5,10b-tetraaza-benzoazulen-5-yl]-ethanone,
- (trans)-8-Chloro-5-methanesulfonyl-1-(4-phenyl-cyclohexyl)-5,6-dihydro-4H-2,3,5,10b-tetraaza-benzoazulene,
- (trans)-8-Chloro-5-isopropyl-1-(4-phenyl-cyclohexyl)-5,6-dihydro-4H-2,3,5,10b-tetraaza-benzoazulene,
- (trans)-8-Chloro-1-(4-phenyl-cyclohexyl)-5-pyridin-2-ylmethyl-5,6-dihydro-4H-2,3,5,10b-tetraaza-benzoazulene,
- (trans)-2-[8-Chloro-1-(4-phenyl-cyclohexyl)-4H,6H-2,3,5,10b-tetraaza-benzoazulen-5-yl]-ethanol, and
- (trans)-8-Chloro-1-(4-phenyl-cyclohexyl)-5-pyridin-2-yl-5,6-dihydro-4H-2,3,5,10b-tetraaza-benzoazulene, or a pharmaceutically acceptable salt thereof.

13. The compound of claim 1, selected from the group consisting of
- (trans)-8-Chloro-1-(4-phenyl-cyclohexyl)-5,6-dihydro-4H-2,3,5,10b-tetraaza-benzo[e]azulene hydrochloride,
- (trans)-8-Chloro-5-methyl-1-(4-phenyl-cyclohexyl)-5,6-dihydro-4H-2,3,5,10b-tetraaza-benzo[e]azulene,
- (trans)-8-Chloro-5-methyl-1-(4-naphthalen-1-yl-cyclohexyl)-5,6-dihydro-4H-2,3,5,10b-tetraaza-benzo[e]azulene,
- (trans)-1-[8-Chloro-1-(4-phenyl-cyclohexyl)-4H,6H-2,3,5,10b-tetraaza-benzoazulen-5-yl]-ethanone,
- (trans)-8-Chloro-5-isopropyl-1-(4-phenyl-cyclohexyl)-5,6-dihydro-4H-2,3,5,10b-tetraaza-benzoazulene,
- (trans)-8-Chloro-1-(4-phenyl-cyclohexyl)-5-pyridin-2-ylmethyl-5,6-dihydro-4H-2,3,5,10b-tetraaza-benzoazulene, and
- (trans)-2-[8-Chloro-1-(4-phenyl-cyclohexyl)-4H,6H-2,3,5,10b-tetraaza-benzoazulen-5-yl]-ethanol.

14. A pharmaceutical composition comprising a therapeutically effective amount of a compound of formula I

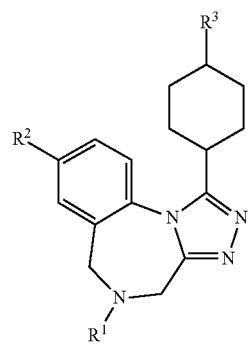

wherein
R¹ is selected from the group consisting of
i) H,
ii) —C₁₋₆-alkyl, unsubstituted or substituted by 1 to 5 substituents individually selected from the group consisting of OH, halogen, cyano and C₁₋₆-alkoxy, iii) —(CH$_2$)$_p$—R$^4$, wherein
  p is 0 or 1,
  R$^4$ is phenyl or 5- or 6-membered heteroaryl, each of which is unsubstituted or substituted by 1 to 5 substituents individually selected from the group consisting of OH, halogen, cyano, C$_{1-6}$-alkoxy, halogen-C$_{1-6}$-alkyl, halogen-C$_{1-6}$-alkoxy and hydroxy-C$_{1-6}$-alkyl,
iv) —S(O)$_2$—C$_{1-6}$-alkyl, wherein the C$_{1-6}$-alkyl is unsubstituted or substituted by 1 to 5 substituents individually selected from the group consisting of OH, halogen, cyano and C$_{1-6}$-alkoxy,
v) —C(O)—C$_{1-6}$-alkyl, wherein the C$_{1-6}$-alkyl is unsubstituted or substituted by 1 to 5 substituents individually selected from the group consisting of OH, halogen, cyano and C$_{1-6}$-alkoxy, and
vi) —C(O)O—C$_{1-6}$-alkyl, wherein the C$_{1-6}$-alkyl is unsubstituted or substituted by 1 to 5 substituents individually selected from the group consisting of OH, halogen, cyano and C$_{1-6}$-alkoxy;
R$^2$ is selected from the group consisting of hydrogen and halogen;
R$^3$ is aryl, unsubstituted or substituted by 1 to 5 substituents individually selected from the group consisting of OH, halogen, cyano, C$_{1-6}$-alkyl, C$_{1-6}$-alkoxy, halogen-C$_{1-6}$-alkyl, halogen-C$_{1-6}$-alkoxy and hydroxy-C$_{1-6}$-alkyl;
or a pharmaceutically acceptable salts thereof and a pharmaceutically acceptable carrier.

* * * * *